US009429743B2

(12) United States Patent
Garsha et al.

(10) Patent No.: US 9,429,743 B2
(45) Date of Patent: Aug. 30, 2016

(54) SYSTEMS AND METHODS OF POLYFOCAL HYPERSPECTRAL IMAGING HAVING A BEAM SPLITTER WITH OPTICAL CHANNELS RESPECTIVELY CORRESPONDING TO PLURAL IMAGE PLANES

(71) Applicants: Karl Garsha, Sahuarita, AZ (US); Michael Otter, Tucson, AZ (US)

(72) Inventors: Karl Garsha, Sahuarita, AZ (US); Michael Otter, Tucson, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 93 days.

(21) Appl. No.: 14/350,463

(22) PCT Filed: Oct. 11, 2012

(86) PCT No.: PCT/EP2012/070157
§ 371 (c)(1),
(2) Date: Apr. 8, 2014

(87) PCT Pub. No.: WO2013/053822
PCT Pub. Date: Apr. 18, 2013

(65) Prior Publication Data
US 2014/0252200 A1 Sep. 11, 2014

Related U.S. Application Data
(60) Provisional application No. 61/546,160, filed on Oct. 12, 2011.

(51) Int. Cl.
| G02B 21/00 | (2006.01) |
| G01N 21/64 | (2006.01) |
| G02B 21/36 | (2006.01) |

(52) U.S. Cl.
CPC ............... *G02B 21/00* (2013.01); *G01N 21/64* (2013.01); *G01N 21/6458* (2013.01); *G02B 21/367* (2013.01); *G02B 2207/113* (2013.01)

(58) Field of Classification Search
CPC .... G02B 21/367; G02B 21/34; G02B 21/00; G02B 21/244; G02B 2207/113; G01N 21/6458; G01N 21/64
USPC .......... 250/559.4, 559.22, 208.1, 216, 201.3; 359/372–377, 368; 356/451–456
See application file for complete search history.

(56) References Cited

U.S. PATENT DOCUMENTS

| 5,591,981 A | 1/1997 | Heffelfinger et al. |
| 5,863,504 A | 1/1999 | Heffelfinger et al. |

(Continued)

FOREIGN PATENT DOCUMENTS

| CN | 1595057 A | 3/2005 |
| EP | 732582 A2 | 1/1999 |

(Continued)

OTHER PUBLICATIONS

Abrahamsson, S. et al., "A new approach to extended focus for high-speed, high-resolution biological microscopy," Proc. of SPIE vol. 6090, 60900N (2006).

(Continued)

*Primary Examiner* — Que T Le
(74) *Attorney, Agent, or Firm* — Charney IP Law LLC; Thomas Finetti

(57) ABSTRACT

A microscope-based system and method for simultaneous imaging of several object planes, of a three-dimensional (3D) sample, associated with different depths throughout the sample. The system includes a polyfocal optical portion, adapted to create a plurality of optical channels each of which is associated with an image of a corresponding object plane, and a spectrally-selective portion, adapted to transform the spectral distribution of the image-forming beam of light to a corresponding spatial distribution. The image, registered by a detector, includes an image of an object plane and an image of the spatially-coded spectral distribution. The method effectuates the simultaneous multispectral imaging of the several object planes. The required data-acquisition time is several fold shorter than that taken by a conventional multispectral microscope-based imaging system.

7 Claims, 22 Drawing Sheets

(56) References Cited

U.S. PATENT DOCUMENTS

| | | | |
|---|---|---|---|
| 6,150,666 | A * | 11/2000 | Engelhardt ............ A61C 19/04 250/216 |
| 6,262,837 | B1 | 7/2001 | Nagano et al. |
| 6,838,650 | B1 | 1/2005 | Toh |
| 7,315,030 | B2 | 1/2008 | Takamizawa et al. |
| 2002/0044346 | A1 | 4/2002 | Nguyen et al. |
| 2006/0017006 | A1 | 1/2006 | Takamizawa et al. |
| 2008/0212866 | A1 | 9/2008 | Lett et al. |
| 2009/0091751 | A1 | 4/2009 | Golovanevsky |

FOREIGN PATENT DOCUMENTS

| | | |
|---|---|---|
| JP | 2006039116 A | 2/2006 |
| JP | 201020298 A | 1/2010 |
| JP | 2010181716 A | 8/2010 |
| WO | 2007095090 A2 | 8/2007 |

OTHER PUBLICATIONS

Carlsson, K., "The influence of specimen refractive index, detector signal integration, and non-uniform scan speed on the imaging properties in confocal microscopy," Journal of Microscopy, vol. 163, Pt 2, pp. 167-178 (1991).

Ford, B., et al., "Computed Tomography-Based Spectral Imaging for Fluorescence Microscopy," Biophysical Journal, vol. 80, pp. 986-993 (2001).

Garsha, K., "Quantitative Fluorescence Microscopy: Considerations and Controls," In: Standardization and Quality Assurance in Fluorescence Measurements II, Springer Series on Fluorescence. Resch-Gener, U. Eds. Springer Berlin, Heidelberg, pp. 55-58 (2008).

Golub, M., et al., "Spectral multiplexing method for digital snapshot spectral imaging," Applied Optics, vol. 48, No. 8, pp. 1520-1526 (2009).

Hibbs, A., et al., "Practical Confocal Microscopy," Handbook of Biological Confocal Microscopy, Third Edition, edited by James B. Pawley, Springer Science, pp. 650-671 (2006).

Malik, Z. et al., "Fourier transform multipixel spectroscopy for quantitative cytology," Journal of Microscopy, vol. 182, Pt. 2, pp. 133-140 (1996).

Ram, S. et al., "High Accuracy 3D Quantum Dot Tracking with Multifocal Plane Microscopy for the Study of Fast Intracellular Dynamics in Live Cells," Biophysical Journal, vol. 95, pp. 6025-6043 (2008).

Schrock, E. et al., "Multicolor Spectral Karotyping of Human Chromosomes," Science, vol. 273, pp. 494-497 (1996).

Swoger, J., et al., "Multiple imaging axis microscopy improves resolution for thick-sample applications," Optics Letters, vol. 28, No. 18, pp. 1654-1656 (2003).

Toprak, E., et al., "Three-Dimensional Particle Tracking via Bifocal Imaging," Nano Letters, vol. 7, No. 7, pp. 2043-2045 (2007).

Speidel, M., et al., "Three-dimensional tracking of fluorescent nanoparticles with subnanometer precision by use of off-focus imaging," Optics Letters, vol. 28, No. 2, pp. 69-71 (2003).

Veldman, T., et al., "Hidden chromosome abnormalities in haematological malignancies detected by multicolour spectral karyotyping," Nature Genetics, vol. 15, pp. 406-410 (1997).

Wagadarikar, A., et al., "Single disperser design for compressive, single-snapshot spectral imaging," Proc. of SPIE., vol. 6714, 67140A-1 (2007).

Wagadarikar, A., et al., "Single disperser design for coded aperture snapshot spectral imaing," Applied Optics, vol. 47, No. 10, pp. B44-B51 (2008).

Wagadarikar, A., et al., "Spectral Image Estimation for Coded Aperture Snapshot Spectral Imagers," Proc. of SPIE, vol. 7076, 707602 (2008).

Wallace, W., et al., "A Workingperson's Guide to Deconvolution in Light Microscopy," BioTechniques, 31, pp. 1076-1097 (2001).

Eismann, et al., "Stochastic Mixture Modeling", In: Chein-I Chang: "Hyperspectral Data Exploitation: Theory and Applications.", Dec. 1, 2008, pp. 107-148.

Burton, et al., "Spectral Optical Imaging in Biology and Medicine", Biomedical Optical Imaging, Apr. 22, 2009, pp. 29-72.

Aguet, et al., "An Introduction to Fluorescence Microscopy", In: Jens Rittscher:"Microscopic Image Analysis for Life Science Applications", Jan. 1, 2008 pp. 85-114.

Stein, "Application of the Normal Compositional Model to the Analysis of Hyperspectral Imagery", Advances in Techniques for Analysis of Remotely Sensed Data, 2003 IEEE Workshop Oct. 27-28, 2003 pp. 44-51.

Pinaud, et al., "Advances in Fluorescence Imaging with Quantum Dot Bio-Probes", Biomaterials, Elsevier Science Publishers vol. 27, No. 9 Mar. 1, 2006 pp. 1679-1687.

Firestone, L. et al., "Comparison of AutoFocus Methods for Automated Microscopy," Cytometry, vol. 12, pp. 195-206 (1991).

Fernandez, C. et al., "Fluorescence microscopy with a coded aperture snapshot spectral imager," Proc. of SPIE vol. 7184, 71840Z (2009).

Prabhat, P., et al., "Simultaneous imaging of several focal planes in fluorescence microscopy for the study of cellular dynamics in 3D," Proc. of SPIE vol. 6090, 60900L (2006).

http://en.wikipedia.org/wiki/Autofocus (Mar. 24, 2014).

http://en.wikipedia.org/wiki/Rangefinder (Mar. 24, 2014).

Official Action issued by the State Intellectual Property Office, P.R. China; Issued Jul. 17, 2015 (translation provided).

* cited by examiner

SYSTEMS AND METHODS OF POLYFOCAL HYPERSPECTRAL IMAGING HAVING A BEAM SPLITTER WITH OPTICAL CHANNELS RESPECTIVELY CORRESPONDING TO PLURAL IMAGE PLANES

TECHNICAL FIELD

The present invention relates to image acquisition and, more particularly, to systems and methods of polyfocal hyperspectral imaging providing images, of a biological sample, characterized by a three-dimensional spatial resolution.

BACKGROUND ART

Image acquisition with a conventional optical imaging system, such as, for example, a microscope used for pathology examination of a biological tissue, has a limited depth of field. In order to acquire imaging data representing a three-dimensional piece of tissue, a conventional image acquisition system has to be configured to allow for sequential imaging of different depths of the tissue sample by either refocusing (along the optical axis, such as z-axis) the optical imaging system at different depths of the sample or, in the case when the focal length of the optical system is fixed, repositioning the optical system with respect to the tissue sample to assure that layers of the sample that are located at different depths are being imaged. In the latter case, the optical imaging system may require a sophisticated automated microscope including an automated repositioning unit such as, for example, an electromechanical adjustor of the optics along the local optical axis.

The situation is complicated even further when spectrally-resolved imaging is at issue, such as fluorescent spectral imaging, because it becomes necessary to take multiple sequential exposures of a given layer of the tissue sample at different wavelengths to build a set of hyperspectral images. The latter inevitably increases costs of image acquisition at least in terms of increased acquisition time, reduced fluorescence due to over-exposure (to illumination) of reporter molecules in the tissue sample, and the need to increase the exposure to compensate for such reduction, and increased computer processing time and the need for large computer-storage capacity. The need exists, therefore, for a method and system of hyperspectral image acquisition, where the quality is not compromised by the abovementioned problems.

SUMMARY OF THE INVENTION

Embodiments of the present invention provide a system, method, and computer program product for use in multi-spectral imaging of a biological tissue with a microscope-based imaging apparatus.

An embodiment of a method for imaging such biological tissue includes receiving, from the microscope, light associated with the tissue and spatially redirecting this light along different optical channels having different corresponding effective optical powers. The embodiment additionally includes detecting light that has transmitted through each of the optical channels with a photodetector in such a fashion as to fill the aperture of the photodetector with images of the tissue formed by these optical channels. In a specific embodiment, the images formed by light passing through different optical channels are formed in different image planes and represent different planes of the tissue that aggregately, define an imaged volume of the tissue. Spatially redirecting the light received from the microscope along different optical channels may include dividing this light with reflectors that are positioned in a spiral and staircase-like relationship with respect to the local optical axis. The embodiment may additionally include filtering light received from the microscope with an optical filter system such as to form spectrally-filtered light the spectrally-different components of which may, optionally, be spatially dispersed, and are detected by the photodetector either in temporal sequence or at a single time point (in parallel). In a specific embodiment, the spectral filtering is carried out such that intensity of spectrally-filtered light at chosen equidistant wavelengths is larger than intensity of light received at an input of the microscope at the same equidistant wavelengths. In a particular implementation, the equidistance wavelengths are chosen such that the distance between them is defined by an optical characteristic of the optical filter system which, optionally, is spectrally-tunable.

Another embodiment provides a method for volumetric imaging of a pathology sample that includes (i) receiving light emanating from object planes that define a volume of the pathology sample and (i) detecting the received light with a photodetector after this light has transmitted through spatially-different optical channels such as to form a volumetric image that includes images of the object planes that are formed on adjacent portions of the photodetector. The volumetric image may optionally include interferometric fringes representing spectral content of light emanating from the object planes. Different optical channels have different effective focal lengths. In a specific embodiment, light received from object planes may be filtered through an optical filter, which is optionally tunable and a spectral transmission characteristic of which is represented by a series of Lorentzian functions. The embodiment may additionally include analysis of the geometrical parameters of the volumetric image to determine the spectral content of the received light.

Embodiments of the invention also provide an optical imaging apparatus. In one implementation, for example, such optical imaging apparatus include an input configured to receive light from a object and in optical communication with a spectrally-selective optical system that is adapted to transmit the received light at spectrally-equidistant wavelengths through spatially-different optical channels onto a photodetector that receives the transmitted light. The light detected by the photodetector fills the photodetector's aperture with images of object planes that are located at different depths of the object and that define the volume, of the object, being imaged. The spectrally-selective optical system may include a device adapted to produce an optical output that contains spatially-coded spectrum of light received at the input. In one implementation, the optical imaging apparatus includes a microscope equipped with a stage that is adapted to support the object being imaged and a positioner configured to change a distance between the stage and a microscope objective. The optical channels may include steerable reflectors.

In another embodiment, the optical imaging apparatus is characterized by multiple image planes and contains a microscope configured to image an object to an intermediate image plane and a Fourier Transform (FT) device that is adapted to receive an image formed at the intermediate image plane and to produce a light distribution corresponding to a Fourier Transform of this image, which contains a spatially-coded spectral content of this image. In a specific embodiment, the microscope includes a stage configured to support the object and a positioner capable of changing the distance separating the microscope objective from the microscope stage, and the FT device includes an interferometer such as, for example, a Sagnac interferometer. The embodiment additionally includes a beam-splitter (BS) device in optical communication with the FT device. The BS device includes a plurality of optical channels respectively corresponding to multiple image planes. Each of these optical channels is configured to re-image the light distribution produced by theft device onto a corresponding image plane such as to form a corresponding image representing a corresponding in-depth layer of the imaged object. The BS device may include adjustable mirrors disposed in a spiral and staircase-like manner around a local optical axis. The embodiment of the invention additionally includes a photodetector configured to detect images representing object layers locate at different depths within the object. In a specific embodiment, the positioner may be motorized and activated to cause at least one of the detected imaged to coincide with a plane of the photodetector.

In yet another embodiment, the multispectral imaging apparatus includes a (i) microscope having an objective and a stage adapted to receive a biological sample; and (ii) a polyfocal image acquisition apparatus in optical communication with the microscope and configured to form images of the biological sample along spatially-different optical channels to which these formed images respectively correspond. The polyfocal imaging acquisition apparatus is configured to form images of the sample at different image planes. The polyfocal imaging apparatus includes a photodetector, and the formed images contain geometrical distributions representing the spectrum of light associated with the biological sample. In a specific embodiment, the polyfocal image acquisition apparatus may be configured to modify these geometrical distributions. The embodiment additionally includes a processor in operable communication with the microscope and the polyfocal imaging apparatus. The processor is programmed to receive imaging data corresponding at least one formed image, and to determine a change of a distance, separating the biological sample positioned on the microscope stage and the microscope objective, that is required to position a predetermined image at a plane of the photodetector. The processor may be additionally programmed to determine a change of the separating distance by subtracting the formed images of the biological sample one from another, assigning to the results of such subtraction corresponding figures of merit that describe intensity characteristics of the resulting subtracted images, and determining the highest figure of merit. A microscope may include a motorized positioner that may be computer-controlled. The processor may be further programmed to cause a change of the separating distance in response to having determined the highest figure of merit such as to position an image corresponding to the highest figure of merit at a plane of the photodetector.

Another embodiment of the invention provides a computer program product for use with a computer-controlled microscope-based imaging system that is adapted for imaging a biological sample and that includes a plurality of spatially-different optical channels. The computer program product includes a tangible digital storage medium which, when loaded into a computer in operable communication with the imaging system, establishes an apparatus that is implemented in the computer and that contains (i) an input configured to receive image data sets representing images of the biological sample, where each of the images having been acquired through a respectively corresponding optical channel from the plurality of optical channels and where different images are formed in different image planes; and (ii) a graphical output configured to display at least one of the images of the biological sample, where each of these images includes a geometrical configuration representing a spectral characteristic of the biological sample. A computer program product may further include an image data processor configured to determine the spectral characteristic of the biological sample by analyzing the displayed geometrical configuration and, in a specific embodiment, additionally be configured to determine figures of merit respectively representing the images and to cause mutual repositioning of the microscope objective and the biological sample based at least on comparison of the determined figures of merit.

BRIEF DESCRIPTION OF THE DRAWINGS

The invention will be more fully understood by referring to the following Detailed Description of Specific Embodiments in conjunction with the Drawings, of which.

DETAILED DESCRIPTION

Figure 1A:
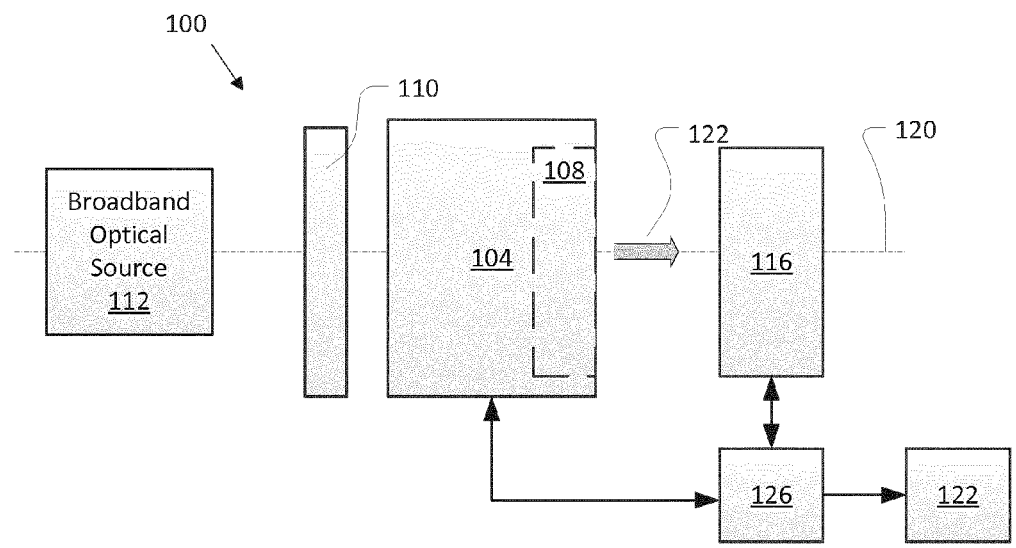
FIGS. 1A and 1B are schematic illustrations of multispectral imaging (MSI) systems for use with the present invention.

References throughout this specification to "one embodiment," "an embodiment," "a related embodiment", or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described features, structures, or characteristics of the invention may be combined in any suitable manner in one or more embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

Method and systems of multispectral polyfocal image acquisition discussed herein result from realization that multispectral imaging of a three-dimensional sample can be carried out simultaneously at multiple focal planes in a manner that does not require mutual repositioning of the imaging optics and the sample. In particular, the proposed method and system are configured to provide, in a single acquisition step and under non-immersion conditions, an image of the sample that contains hyperspectral imaging data corresponding to sample layers that are located at different depths within the sample with a several-fold increase in the field-of-view (FOV) and with about 16 time increase of the depth of field (DOF) as compared with a conventional single focal plane, full-field spectral data acquisition of an oil-immersed tissue image with a 100×-microscope. As a result, numerous shortcomings associated with conventional hyperspectral-imaging systems are alleviated or eliminated. Specifically, embodiments of the disclosed invention allow to bypass repetitive mechanical movement associated with mutual repositioning of imaging optics and the images sample, assures shorter imaging cycles, and preserves photolabile counterstains or other chemical moieties that may be associated with the imaged sample by substantially reducing sample-photobleaching effects due to reduction of photo-exposure required to collect a predetermined multispectral imaging data at numerous focal planes. In addition, embodiments of the invention allow to increase the accuracy of depth determination within the sample, which is significant when imaging is carried out with dry objectives.

Conventional Multi-Spectral Imaging Systems and Embodiments of the Invention

Embodiments of the present invention may be employed with an imaging system such as a multispectral imaging (MSI) system or a fluorescent microscopy system. MSI, generally, equips the analysis of pathology specimens with computerized microscope-based imaging systems by providing access to spectral distribution of an image at a pixel level. While there exists a variety of multispectral imaging systems, an operational aspect that is common to all MSI systems is a capability to form a multispectral image. A multispectral image is one that contains image data captured at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR).

Figure 1B:
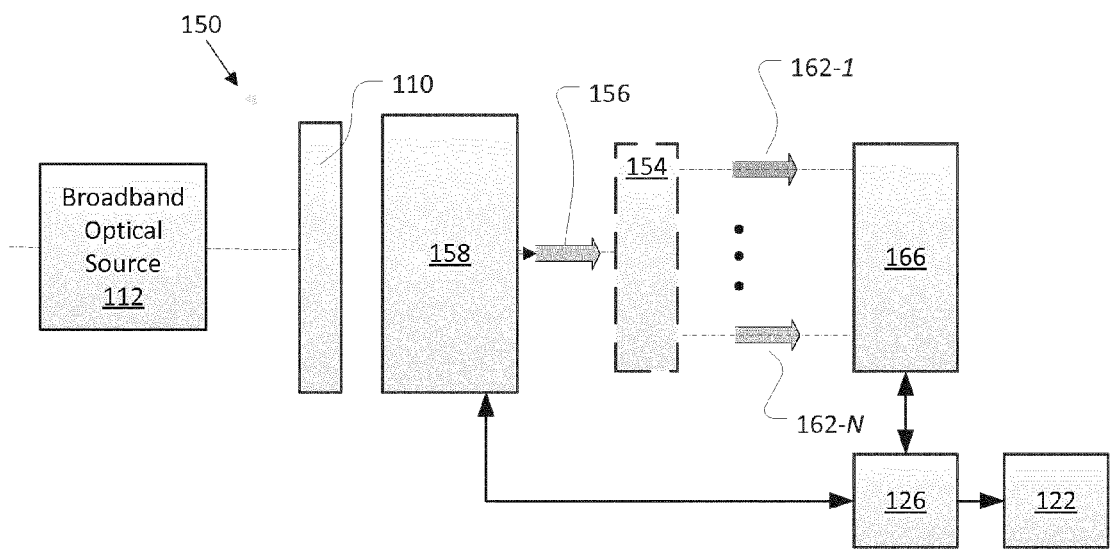

Two common types of an MSI system facilitating the acquisition of images of a specimen are schematically illustrated in FIGS. 1A and 1B. FIG. 1A shows an apparatus 100 including an optical imaging system 104, a portion 108 of which contains a spectrally-selective system that is tunable to define a pre-determined number N of discrete optical bands. The optical system 104 is adapted to image a tissue sample 110, illuminated in transmission with a broadband light source 112 onto an optical detector 116. As shown, the optical imaging system 104, which in one embodiment may include a magnifying system such as, for example, a microscope, has a single optical axis 120 generally spatially aligned with a single optical output 122 of the optical system 104. The system 104 forms a sequence of images of the tissue 110 as the spectrally-selective system 108 is being adjusted or tuned (for example with a computer processor 126) such as to assure that images are acquired in different discrete spectral bands. The apparatus 100 may additionally contain a display 122 in which appears at least one visually-perceivable image of the tissue from the sequence of acquired images. The spectrally-selective system 108 may include an optically-dispersive element such as a diffractive grating, a collection of optical filters such as thin-film interference filters or any other system adapted to select, in response to either a user input or a command of the pre-programmed processor 126, a particular pass-band from the spectrum of light transmitted from the light source 112 through the sample 110 towards the detector 116.

An alternative implementation 150 of an apparatus adapted to simultaneously take a multiplicity of spectrally-discrete optical images in several spectral bands is shown in FIG. 1B. Here, the spectrally-selective system 154 defines several optical outputs corresponding to N discrete spectral bands. The system 154 intakes the transmitted light output 156 from the optical system 158 and spatially redirects at least a portion of this light output along N spatially different optical paths 162-1 through 162-N in such a way as to image the sample 110 in an identified spectral band onto a detector system 166 along an optical path corresponding to this identified spectral band. It is appreciated that another alternative embodiment (not shown) may combine features of the embodiments 100 and 150.

In a specific embodiment, however, the multi-spectral content of imaging information about the 3D tissue sample is determined by transforming the imaging data, acquired in a single acquisition step with the use of a microscope characterized by a DOF, into a spatial-frequency domain to form spectrally-resolved imaging data. In addition, the 3D-content (polyfocal content) of acquired data is determined by transforming the imaging data spatially via separating or decoupling portions of imaging signal, that correspond to different depths of the sample within the DOF of the microscope objective, with the use of multi-channel imaging optics having different focal lengths and, optionally, light-steering elements to form polyfocal imaging data.

As discussed below, one subsystem (referred to herein after as a "spectral device" and that facilitates a process of spectrally-resolving imaging data) and another subsystem (referred to as "polyfocal optics" or "polyfocal optical portion" that facilitates the process of spatially-resolving the imaging data) are, generally, independent from one another and the use of one does not necessarily restrict the use of another. Moreover, both of the subsystems can be engaged at the same time.

Polyfocal (spatially-resolved) and spectrally-resolved imaging data, obtained by imaging a biological sample with an embodiment including both subsystems, form a four-dimensional data set representing a multispectral image of a 3D sample. The spectrally-resolved and polyfocal portions of the imaging signal are further simultaneously registered with a single optical detector such as a CCD. As a result, in the plane of the detector there is formed a superposition of an image portion containing spatially-transformed imaging data (that provides spatial description of a particular in-depth layer of the imaged sample) with an image portion containing spectrally-resolved data (and that provides spectral content of that particular sample layer). The spectral and spatial parameters describing each of the represented depths of the sample are then determined from the corresponding polyfocal and spectrally-resolved image portions, and optionally stored on a tangible, non-transient computer-readable medium for further processing, and, if required, displayed to the user.

Alternatively, any of the subsystems can be structurally and optically disengaged if required. As a result of acquiring the optical imaging data with an embodiment containing polyfocal optics but from which a spectral device is disengaged, the optical detector registers an image of multiple spatially-different object planes at an operational wavelength of choice. On the other hand, as a result of acquiring the optical imaging data with an embodiment containing a spectral device but from which the polyfocal optical portion is removed, the detector registers an image of a single object plane at numerous spectral bandwidths defined by the spectral device.

Figure 2:
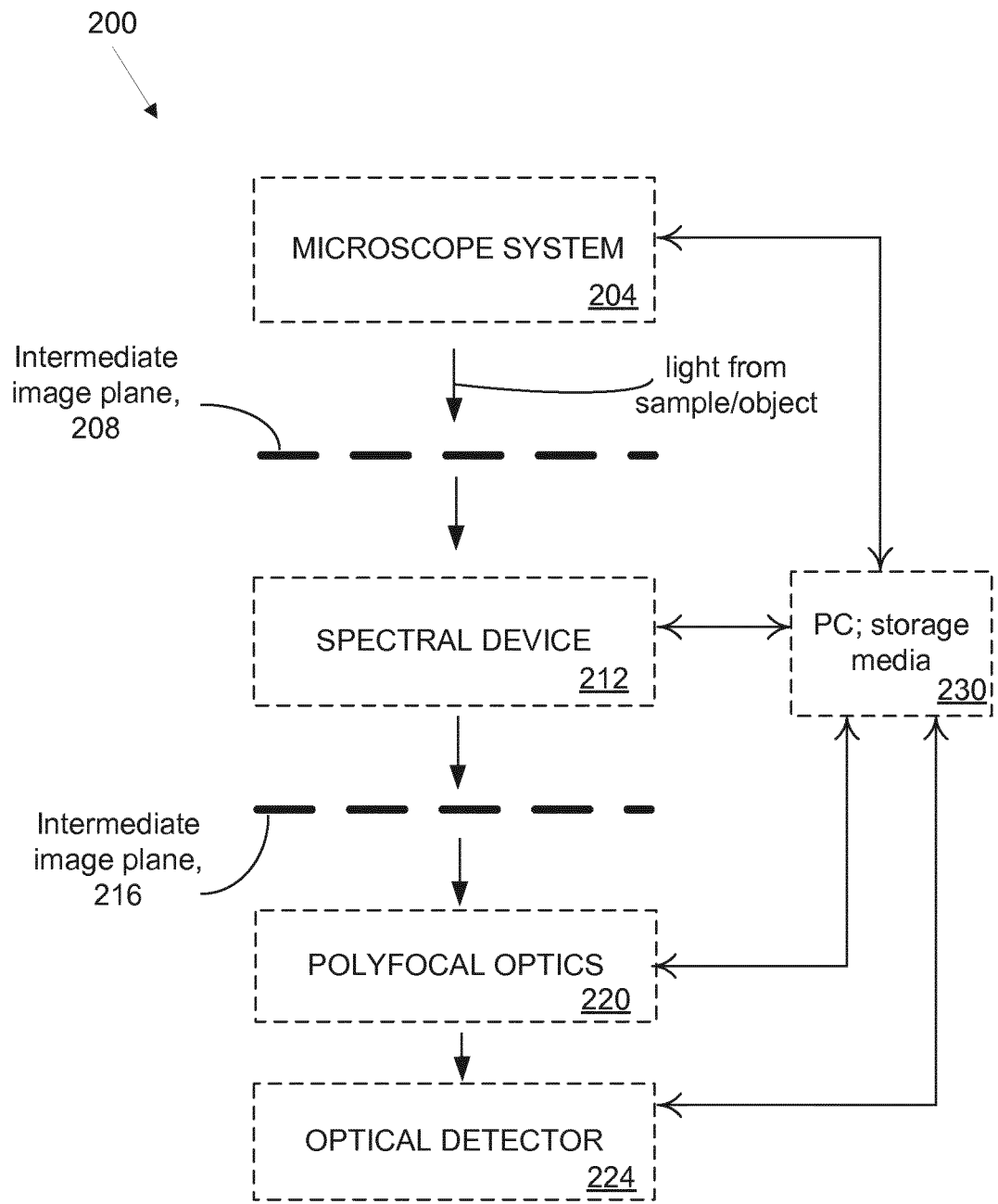
FIG. 2 is a schematic showing a microscope-based imaging system according to an embodiment of the invention.

Generally, the microscope, the spectral device, and the polyfocal optics are mutually cooperated to form an optical train of sequentially-positioned optical subsystems that relay light forming the imaging data from a sample being imaged to the optical detector. In one embodiment, such optical relay includes forming at least one intermediate image of the sample in a corresponding intermediate image plane. FIG. 2 provides a schematic illustration to a concept of a polyfocal hyperspectral imaging system of the invention, showing a microscope system 204 imaging an object onto a first intermediate image plane 208; a spectral device 212 relaying an intermediate image from the first plane 208 to a second intermediate plane 216; and polyfocal optics 220 re-imaging an intermediate image formed at the second intermediate image plane 216 onto an optical detector 224, all optionally controlled and coordinated with a computer system 230 that is equipped with a program code and corresponding storage medium.

Imaging System

Figure 3:
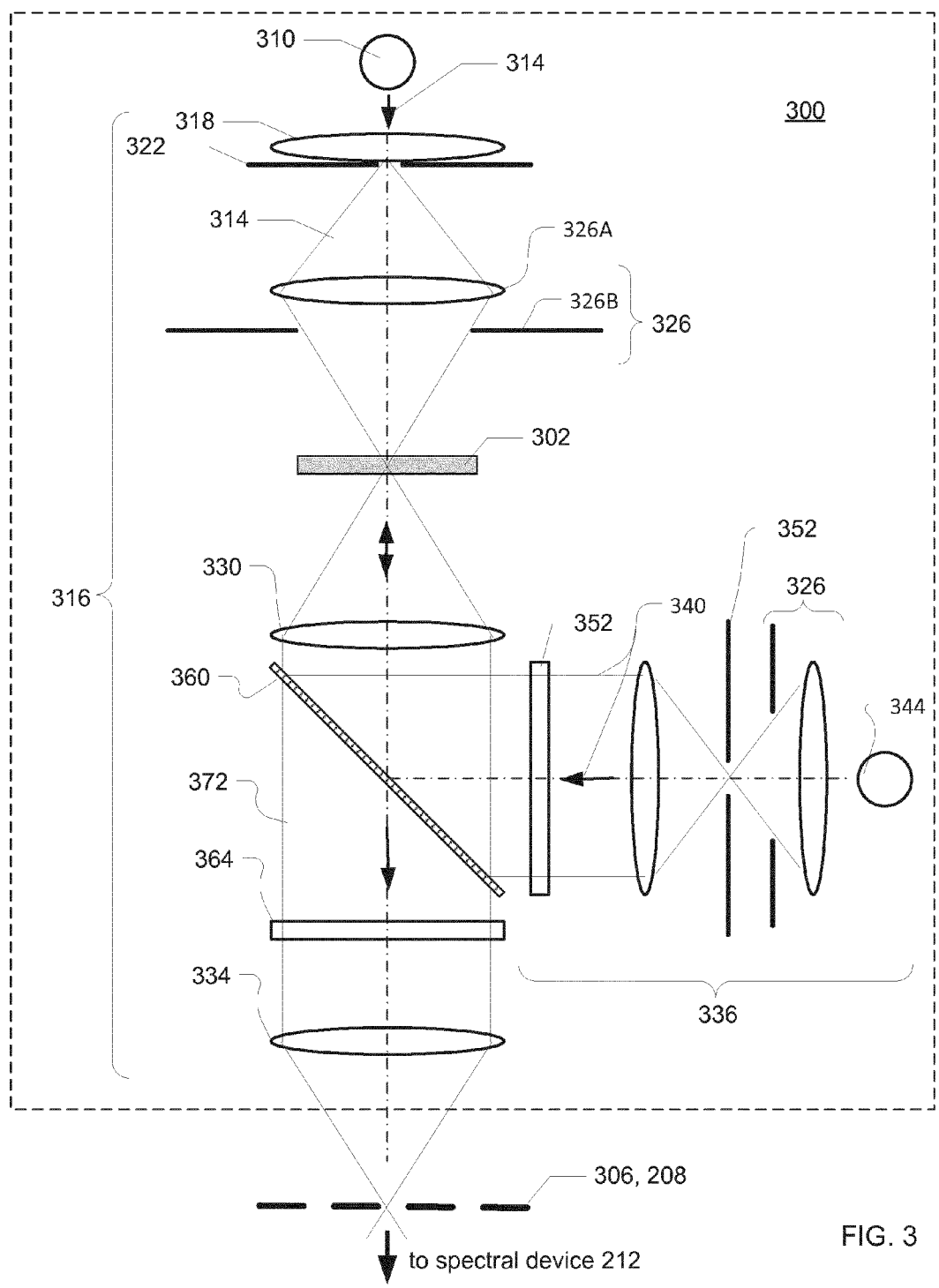
FIG. 3 is a schematic of an embodiment of the microscope portion of the imaging system of the invention.

FIG. 3 illustrates an embodiment 300 of the microscope subsystem 204 of FIG. 2, used to image a sample/object 302 onto a first image plane 306. The embodiment 300 includes an illumination source 310 transmitting light 314 through an optical train 316 onto the intermediate image plane 306. As shown, the first optical train 316 has a field lens 318, a field aperture 322, a first condenser 326 (shown to include a first condenser lens 326A and a first condenser aperture 326B), an objective lens 330, and a tube lens 334. The embodiment 300 additionally includes an illuminator 336 that is adapted to illuminate, through the objective lens 330, the sample 302 with excitation light 340 from a second illumination source 344. The illuminator 336 is configured to ensure that illumination of the sample 302 with the excitation light 340 is causes the sample 302 to fluoresce. This fluorescent emission from the sample 302 is collected with the objective lens 330 and further redirected towards the tube lens 334. The illuminator 336 contains a second illumination source 344, a second condenser 348, a second field aperture 352, and an excitation filter 356 adapted to select (in one implementation—tunably) spectral content of the excitation light 340. In a specific embodiment, the second field aperture 352 is rectangular.

A beam-splitter 360 is appropriately positioned at an intersection of the optical beams propagating through the optical train 316 and the illuminator 336 such as to ensure at least partial spatial overlap between these optical beams. An emission filter 364, that is removably disposed across the image-forming beam 372 between the beam-splitter 360 and the tube lens 334, is configured to transmit the fluorescent optical signal from the optically-excited sample 302 towards the tube lens 334 and to block illuminating light beam 340. The optical system of the embodiment 300 is appropriately adjusted to ensure that the image of the second field aperture 352 is relayed to the intermediate image plane 306. In one embodiment, the microscope may include a Kohler illumination system. Generally, however, other illumination systems known in the related art may be appropriately used.

Moving along the optical train of the system of the invention and in further reference to FIGS. 2 and 3, an embodiment of the spectral device 212 is configured to relay an intermediate image of the object (such as the object 302 of FIG. 3) formed at the intermediate image plane (such as the image plane 208 or the plane 306) onto another intermediate image plane (such as the plane 216) that is located in front of the polyfocal optics 220. Embodiments of the spectral device 212 will be discussed elsewhere in this application.

Polyfocal Optical Portion

As discussed below, embodiments of the polyfocal optical portion of the system of the invention facilitate reduction of time needed for an acquisition of an image of 3D object (such as a piece of pathological tissue, for example) and permit the simultaneous acquisition of imaging data representing multiple object planes that are imaged, generally, at multiple image planes corresponding to different optical channels of the polyfocal optical portion.

1) Pure Polyfocal

Figure 4:
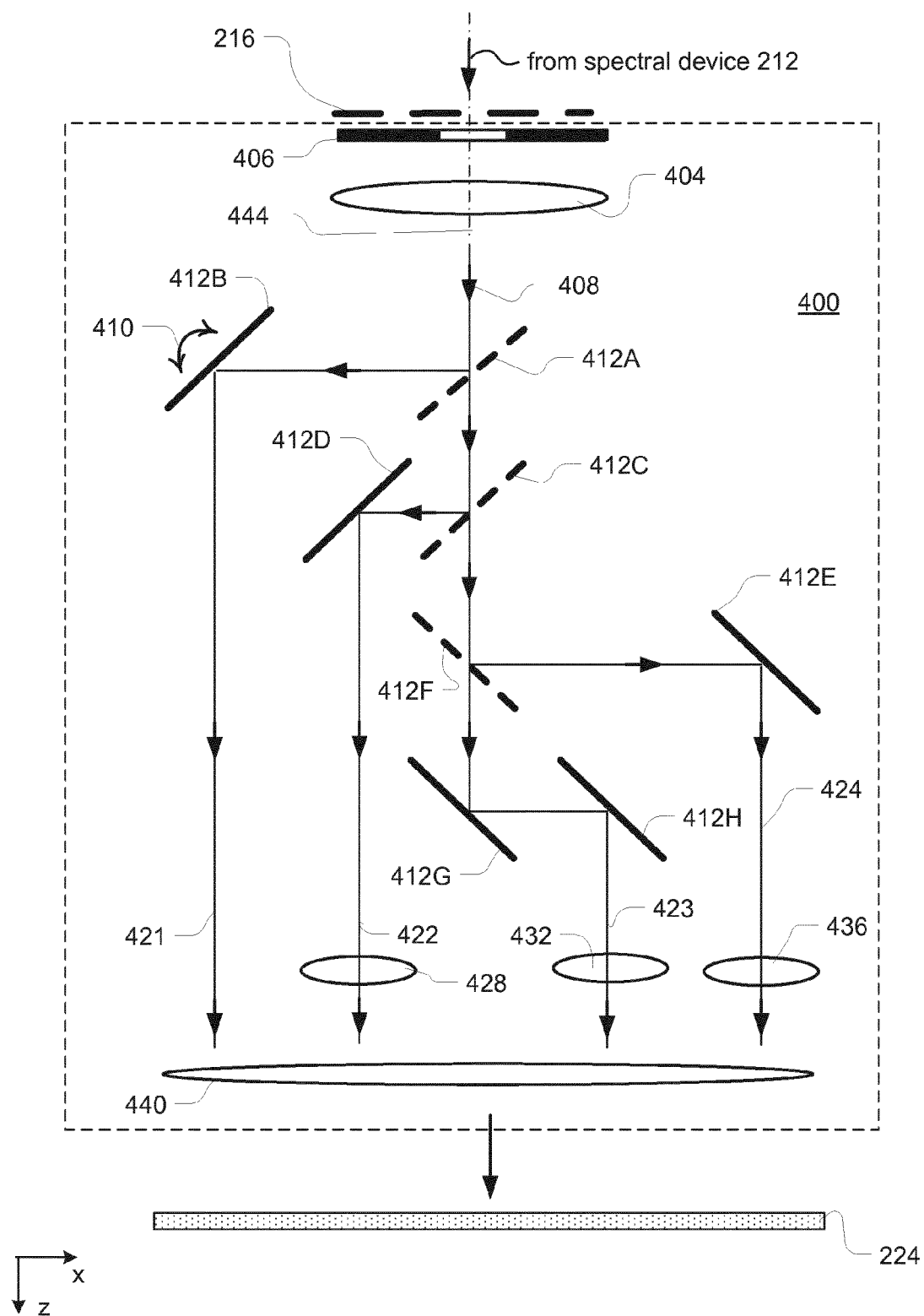
FIG. 4 is a schematic of an embodiment of a polyfocal optical portion of the system of the invention.

An embodiment 400 of the polyfocal optical portion 220 of the system of FIG. 2, re-imaging an intermediate image from the plane 216 onto the target image planes in front of the optical detector 224, is now described in reference to FIG. 4.

An input of the polyfocal optics portion 400 is equipped with a collimating lens 404 to receive light, from the second intermediate image plane 216 through a preferably rectangular aperture 406, and to transmit the received light as a collimated beam 408 towards a group of steering mirror elements. The steering mirror elements denoted 412A, 412B, 412C, 412D, 412E, 412F, 412G, and 412H are appropriately positioned to define generally a plurality of (as shown, four) optical channels and to split the incoming collimated beam 408 into a corresponding number of image-forming beams (as shown, four beams 421, 422, 423, and 424) each of which is directed along a corresponding optical channel. At least some of the image-forming beams (as shown, the beams 422, 423, and 424) are further transmitted towards corresponding adjustment lenses 428, 432, 436. Light from the image-forming beams 421, 422, 423, and 424 is further received by a final imaging lens 440 that forms, at a plane of the optical detector 224, sub-images (not shown) respectively corresponding to the image-forming beams 421, 422, 423, and 424.

Implementations of the idea of polyfocal imaging according to the present invention allow for imaging of multiple object planes while preserving the spatially-fixed cooperation among the detector of the microscope-based imaging system, the optics of the system, and the sample under test. Generally, if a detector is spatially fixed with respect to the optics of the microscope and the sample, the detector registers a 2D optical image of a particular object plane that is defined, in part, by the focal length of the microscope objective. For example, an embodiment 500 of FIG. 5A (which, in comparison with the embodiment 200 of FIG. 2, does not have the polyfocal optical portion 220), is structured to produce an image of a particular portion of the object that is "in focus" at the time of the image data acquisition. Similarly is formed an image by the embodiment 550 of FIG. 5B (which, in comparison with the embodiment 200 of FIG. 2, has neither the spectral device 212 nor the polyfocal optical portion 220). Embodiments of the present invention are also generally structured such that the location of the plane of the detector is fixed with respect to the optics of the microscope. Therefore, in order to enhance an embodiment with the polyfocal imaging capability, and in further reference to FIGS. 2, 3 and 4A, optical characteristics of adjustment lenses 428, 432, 436 are appropriately chosen to differ from one another. As a result, the individual imaging channels of the system (as shown, the channels corresponding to image-forming beams 421, 422, 423, and 424, along which the light is transmitted towards the detector 224 from the sample 302 through the lenses 330, 334 and the adjustment lenses) image different layers, depth-wise, of the sample 302. In a specific embodiment, focal lengths of the adjustment lenses 428, 432, 436 are chosen to assure that effective focal lengths of optical trains respectively corresponding to the imaging beams 421, 422, 423, 424 are different and that different object layers are imaged onto corresponding different image planes.

Figure 5A:
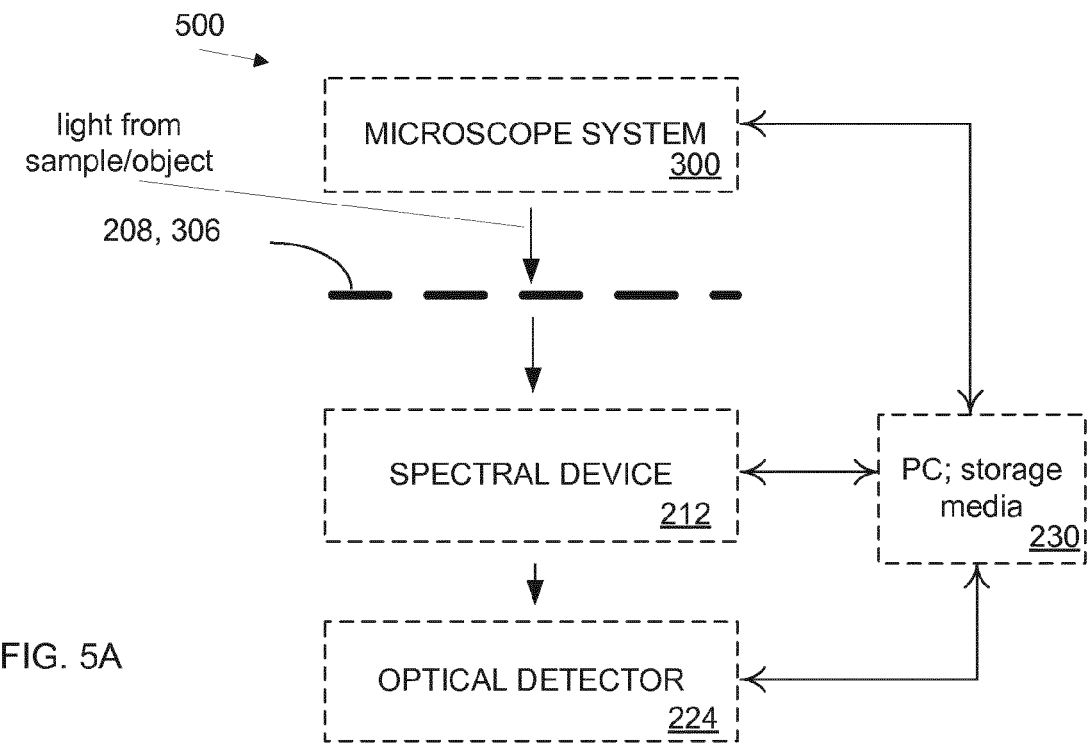
FIGS. 5A, 5B, and 5C are schematics showing embodiments that include specific portions of the system of FIG. 2.
Figure 5B:
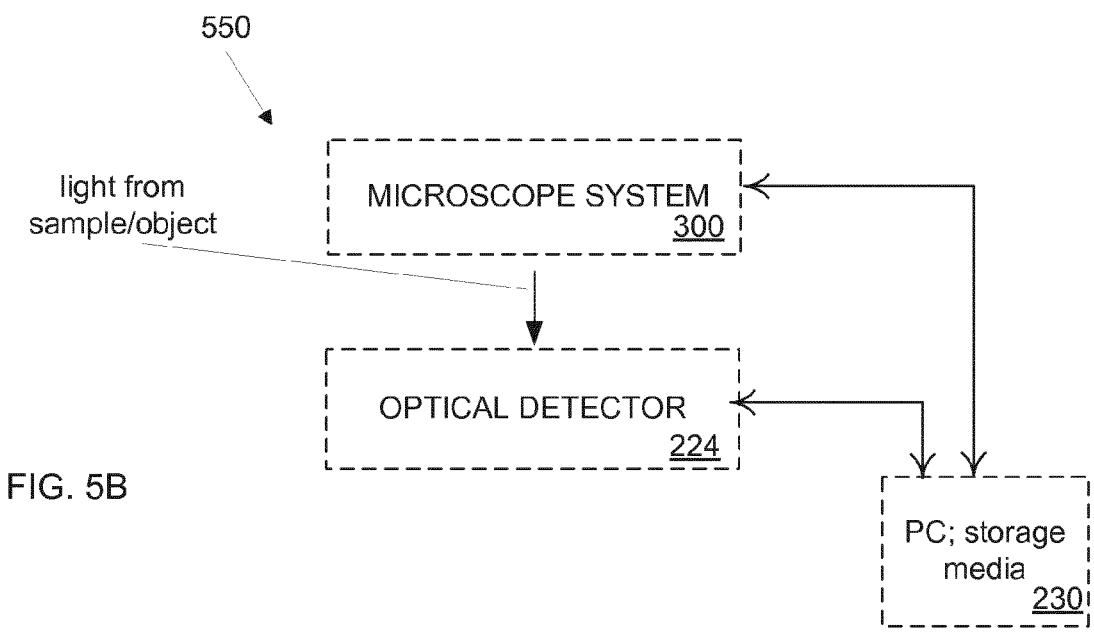
Figure 5C:
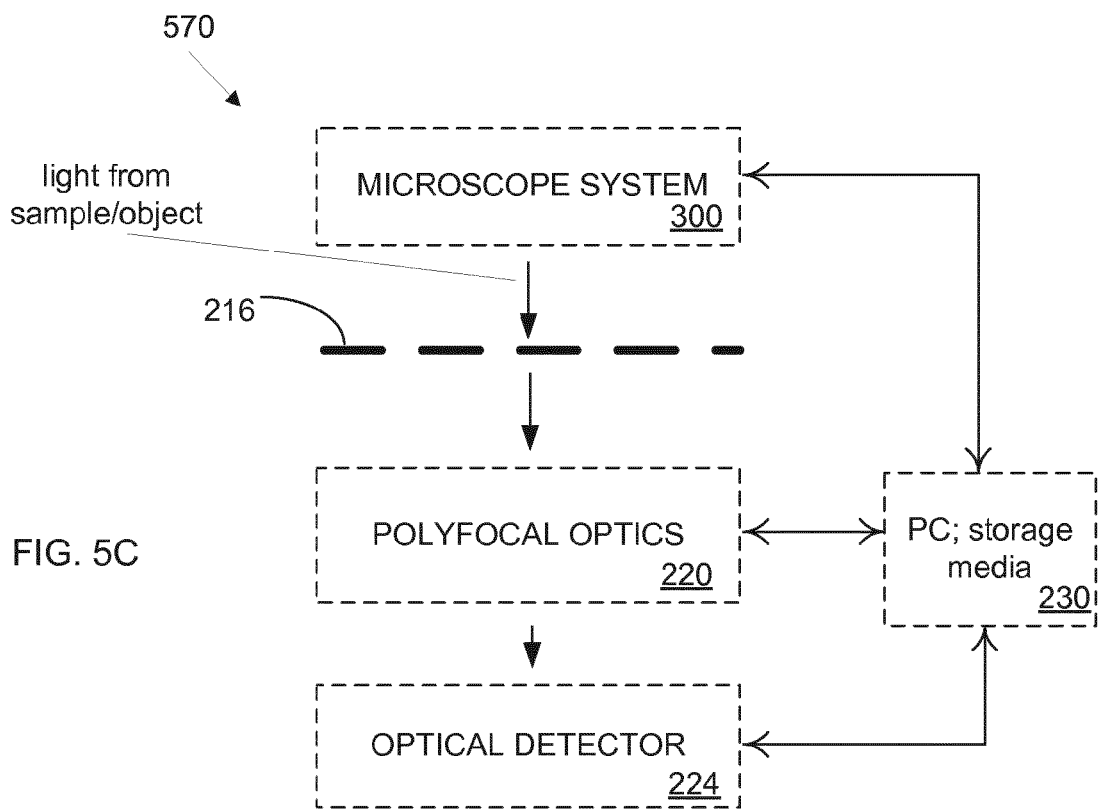
Figure 6:
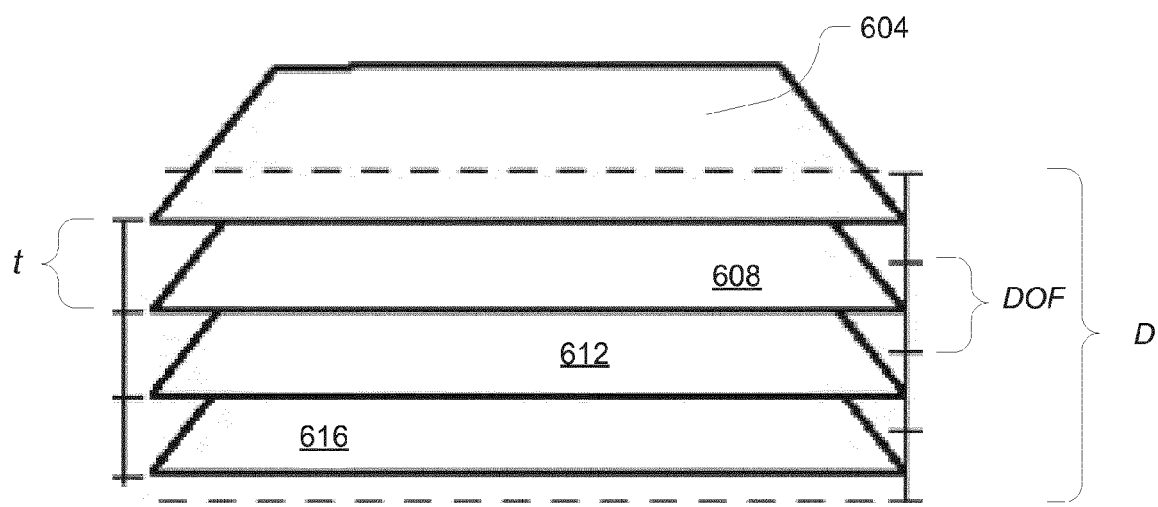
FIG. 6 is an illustration of depth-of-field characteristics of the embodiment of FIG. 2 in relation to object planes imaged with such embodiment.

The idea of polyfocal imaging of the present invention is further illustrated in reference to the diagram of FIGS. 5C and 6 and in further reference to FIGS. 2, 3, and 4A. The diagram of FIG. 6 depicts a plurality of sequential object planes (respectively corresponding to a plurality of layers of the imaged sample) that can be imaged simultaneously with the use of the embodiment 200 of FIG. 2 equipped with the microscope 300 of FIG. 3 and the polyfocal optics 400 of FIG. 4A. If the effective focal lengths of the adjustment lenses of the embodiment 400 differ from one another by t, for example, and if the objective lens 330 has a depth-offield DOF, the effective depth of field within which the sample can be imaged is enhanced from DOF to D, as compared with a conventional imaging system that is devoid of such adjustment lenses. Aggregately, the four imaging channels are adapted, therefore, to image four different layers 604, 608, 612, and 616 of the sample 302 that are equidistantly spaced, by t, in-depth of the sample. For example, for t=2 microns and DOF=2 microns, the effective depth-of-field of the polyfocal embodiment of the invention is D=8 microns.

In further reference to FIG. 4, the polyfocal optical portion 400 includes steering mirrors 412A, 412B, 412C, 412D, 412E, 412F, 412G, and 412H and the corresponding adjustment lenses 428, 432, 436. The steering mirrors and the adjustments lenses are spatially arranged in a spiral and staircase-like manner with respect to the local optical axis 444 of the incoming beam 408 (that is parallel to the z-axis of FIG. 4) such that sub-images 721A, 722A, 723A, and 724A, shown in FIG. 7 and respectively formed by the light beams 421, 422, 423, 424, are adjacent in the plane of the detector 224.

Optionally, the spatial orientation of at least some of the steering mirror elements is kinematically adjusted, as shown by an arrow 410 for the mirror 412B. In one embodiment, some of the steering mirrors 412A, 412B, 412C, 412D, 412E, 412F, 412G, and 412H are partially transparent (as indicated by dashed lines) to effectuate division of the intensity of the incoming beam 408 among the image-forming beams according to desired ratios.

Reconfigurable Field of View

Figure 7:
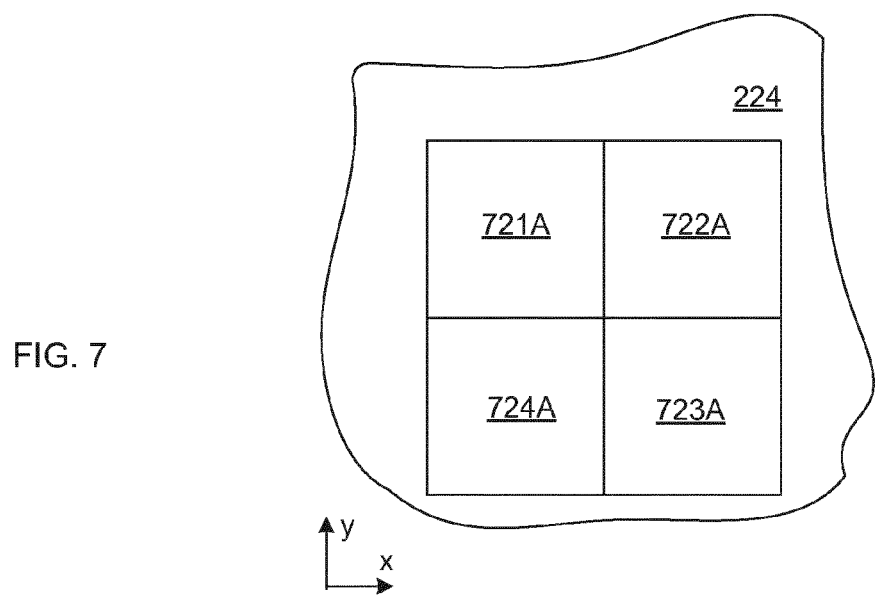
FIG. 7 is a schematic showing mutual positioning of sub-images formed, at the detector, by image-forming light transmitted through the optical channels of the polyfocal optical portion of FIG. 4.

In order to ensure that polyfocal imaging of N object planes onto a single detector produces non-overlapping images, the rectangular aperture is placed into the optical path. Such aperture is appropriately dimensioned to transmit light corresponding to 1/N part of the full FOV of the objective lens 330 of FIG. 3. For example, in the embodiment of FIG. 4, which is adapted to image simultaneously N=4 object planes that respectively correspond to optical trains transmitting light beams 421, 422, 423, 424, the rectangular aperture 406 is dimensioned to frame about 25% of the FOV of the lens 330. The resulting sub-images 721A, 722A, 723A, and 724A shown of FIG. 7 are dimensioned to occupy respective quadrants of the single camera chip 224.

Figure 8A:
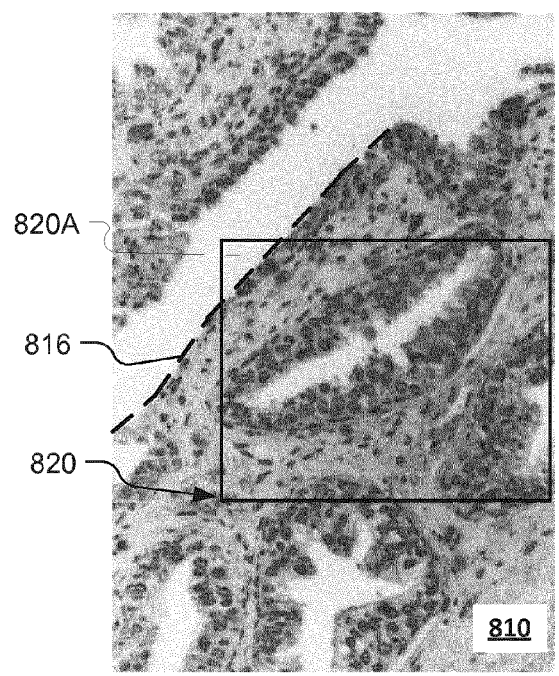
FIGS. 8A and 8B are images of an irregularly-shaped region of interest (ROI) overlapped with boundaries defining a FOV of a conventional imaging system and that of an embodiment of the polyfocal imaging system, respectively.
Figure 8B:
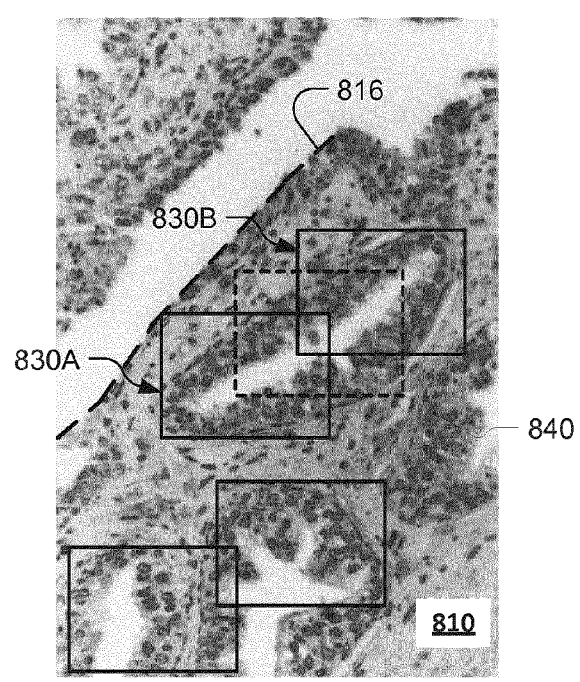

As a corollary advantage provided by an embodiment of the polyfocal imaging system of the invention is the ability of the system to efficiently acquire images of irregularly-shaped ROIs. In particular, efficient imaging of an irregularly-shaped object feature (especially one that is larger than the FOV of the used imaging system) onto a rectangular detector usually results in either overimaging (when a portion of the image falls outside of the detector) or underimaging (when a portion of the detector registers the background and not the image of the ROI). As shown in FIG. 8A, for example, imaging of an ROI 810 having an irregular boundary 816 with a conventional microscope-based system that does not possess the polyfocal-imaging capability described in this application, results in forming an image 820 a portion 820A of which is occupied by the background outside of the ROI 810. In contradistinction, imaging of the sample of interest with an embodiment of the polyfocal imaging system allows to take sequentially images 830A, 830B and the like at a FOV that is reduced in proportion to the number of imaging channels. Formed images aggregately cover the ROI 810 while following the irregular boundary 820A without crossing it, as shown in FIG. 8B. Consequently, embodiments of the invention facilitate the efficiency of acquiring comprehensive imaging data representing the irregularly-shaped objects while minimizing the acquisition of irrelevant imaging data.

Furthermore, because the FOV of an embodiment of the polyfocal imaging system of the invention is reduced in comparison with the conventional system, photobleaching of pathology specimens in the context of fluorescent imaging is significantly reduced. Indeed, efficient photoactivation of fluorescent elements or intentional photobleaching of the sample is restricted to small control areas (such as area 840 of FIG. 8B, shown with a dashed line) that are defined by overlapping FOVs corresponding to different exposures. This fact may be advantageously used for polyfocal spectral FRET, in which multiple acquisitions may be required to measure the efficiency of the resonant transfer of energy with acceptor photobleaching.

It is appreciated that imaging with an embodiment of the invention can be carried out with a larger FOV by re-configuring the system to change optical magnification. For example, if an object field imaged with the use of a polyfocal imaging system of the invention at 100× magnification is 1,384 square microns, at a 40× magnification the same system will image an area of 8,652 square microns, and at 10× magnification the captured object area increases to 138,445 microns. Alternatively, a larger sensor (CCD or CMOS, for example), or a combination of a larger sensor with a larger objective (such as a stereomicroscope/microscope objective) can be used to increase the size of the FOV.

In addition, in further reference to FIG. 2, an embodiment of the invention is adapted to allow a disengagement (or by-passing) of the polyfocal optics portion 220 and, thereby, a re-imaging of an intermediate image from the plane 216 directly to the plane of the detector 224. The reconfiguration of the system resulting in disengagement or by-passing of the polyfocal optics portion 220 includes two steps. At first step, the aperture that restricts the FOV (for example, the aperture 406 of FIG. 4) is moved away from the path of the image-forming optical beam 408. Following the removal of the FOV-limiting aperture, the assembly holding the beam-splitting mirrors 412B, 412D, and 412H of FIG. 4 is coordinated to remove these beam-splitting mirrors such as to retain a single optical path (corresponding, in the example of FIG. 4, to a beam propagating along the optical axis 444. In an alternative embodiment, an auxiliary opaque reflector (a mirror or a prism, for example, not shown) is inserted into the optical path of the beam 408 prior to the first beam-splitting mirror 412A to redirect the beam 408 along a single optical path around the beam-splitting optics.

As a result of such advantageous reconfiguration, an embodiment is adapted to operate either as a conventional imaging system of FIG. 5A that is equipped to acquire a single object plane with a maximum FOV or as a polyfocal imaging system equipped to image simultaneously each of the N object planes at 1/Nth portion of the maximum FOV. The disengagement of the polyfocal optics portion 220 of an embodiment (resulting in a structure schematically shown in FIG. 5A) proves to be advantageous during the multispectral image data acquisition utilizing the spectral device 212 as discussed below, when the required exposure time is significantly longer than the step of spectral tuning of the spectral device (for example, the step rate of the interferometer). An another example, it may be desirable to disengage the polyfocal optics portion 220 of the system when imaging of a large FOV is required at very high resolution, or when the sample at hand is thin and can be efficiently represented by imaging a single object plane.

2) Hybrid-Polyfocal

The above-discussed embodiments of the invention configured for polyfocal image acquisition are structured to image simultaneously multiple object planes and, as a result, are operable to gather very efficiently the molecular probe data through the thickness of a pathological sample (such as a 3D sample of a biological tissue) in a single snap-shot, without mechanical movements required by conventional systems to traverse a thickness region of the sample. Various spectral imaging technologies such as those applied to molecular pathology (for example, to evaluate multiplexed quantum dot (QD) FISH assays such as TMPRSS2:ERG insertion assays) significantly benefit from the resulting shortening of imaging cycles. The described polyfocal imaging technique is pertinent in the context of conventional brightfield ISH (in-situ hybridization) and chromogenic assays as well because of the need to distinguish probe localizations in 3D space and to capture images with extended depth of field. The described polyfocal imaging technique can be adapted to color-camera image acquisition by, for example, using a camera designed for RGB color imaging (such as Bayer mask or 3-CCD cameras, for example) or, alternatively, by employing sequential exposure using red, green and blue color filters in either the transmitted light path or detection path, or by selection of red, green and blue wavelength bands from hyper-spectral data. Embodiments of the invention implement fewer electromechanical and/or automated components than conventional automated microscope system equipped with axial repositioning capabilities. Nevertheless, a combination of the described above polyfocal acquisition system with a conventional z-stepping means has a potential to increase even further the number of object planes that can be imaged in a given amount of time or, alternatively, to reduce the time of image acquisition.

Accordingly, a related embodiment of the invention incorporates a conventional axial stepping (z-stepping) means such as a micromotor that is operable to advance the objective lens of the microscope with respect to the object/sample, or alternatively, to move the sample with respect to a fixed lens. In this case, the number of in-depth object planes that can be imaged in a unit of image-acquisition time is increased even further. This "hybrid" polyfocal-stepping approach can be used to acquire spatially-interlaced stacks of object layers to achieve higher axial resolution while imaging the entire thickness of the sample. Alternatively, this hybrid approach can facilitate increasing the dynamic range of thickness of the sample that can be imaged in a given number of acquisition events. The first application is schematically illustrated in FIG. 9, while the second application is depicted in FIG. 10.

Figure 9:
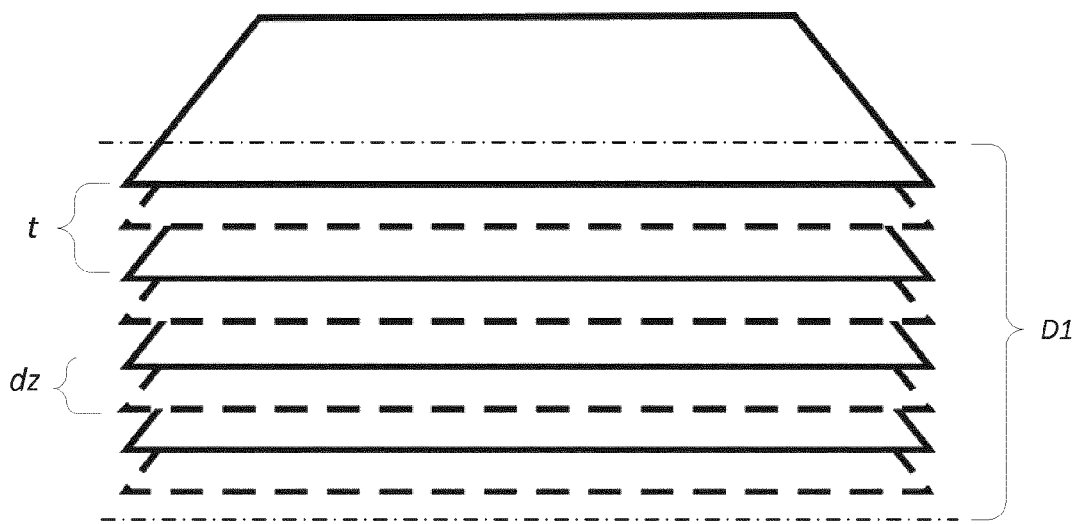
FIGS. 9 and 10 are schematics illustrating thicknesses of the biological sample that can be imaged with an embodiment of the invention equipped with an axial-stepping means.
Figure 10:
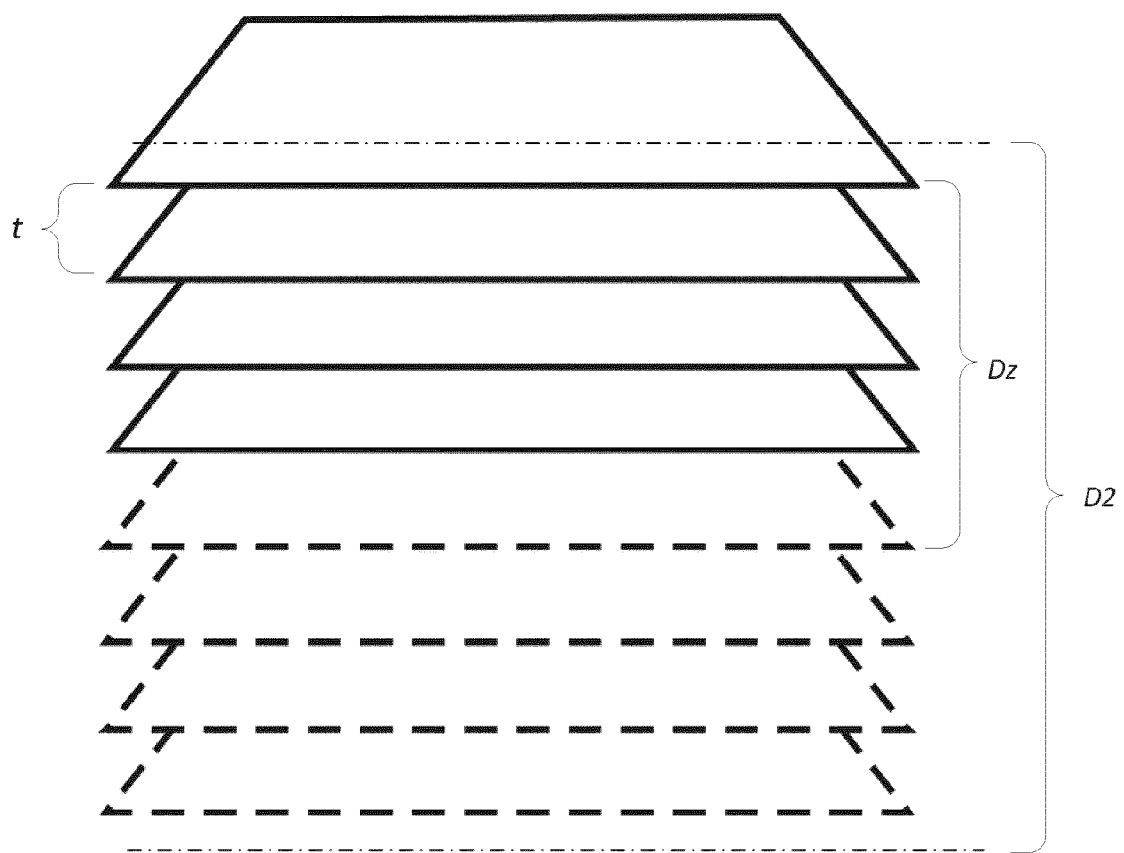

As shown in FIG. 9, a combination of the conventional stepping with an axial increment of dz and the polyfocal imaging system described in reference to FIG. 6 allows to collect, at two consecutive z-positions of the objective, polyfocal imaging data representing sets A and B of object in-depth planes that are spatially interleaved. The object planes of set A imaged at the first position of the objective lens 330 of FIG. 3 are shown in solid lines, and the object planes of set B imaged at the second position of the objective lens 330 of FIG. 3 are shown in dashed lines. In the time window that a conventional microscope 300 equipped with an axial-stepping means needs to acquire spectral imaging data corresponding to two in-depth layers of the object at two dz-spaced positions of the objective, eight different object layers are imaged with a specific "hybrid" embodiment combining the same microscope and the polyfocal optics 400. The overall thickness of the object imaged during this time-window by the hybrid polyfocal embodiment substantially amounts to D1. As an example, in a specific embodiment with t=2 microns and dz=1 micron, D1 equals 9 microns. It is appreciated that the hybrid polyfocal-stepping image acquisition system facilitates increase in efficiency and axial resolution with which stacks of object layers can be imaged through the entire thickness of the specimen.

Alternatively, the same device combination can increase the overall imaged depth of the object from D1 to D2 when the axial increment of the stepping motor is increased from dz to Dz. In reference to FIG. 10, a first set of individual object planes (shown in solid lines) is imaged at a first position of the microscope objective. A second set of individual object planes (shown in dashed lines) is imaged at a second position of the objective (with respect to the object) that differs from the first position by Dz. As a result, at two consecutive positions of the objective lens of the microscope with respect to the object the aggregate depth D2 of the object can be imaged. As an example, in a specific embodiment with t=2 microns and Dz=8 micron, D2 equals 16 microns. Therefore, the hybrid polyfocal-stepping embodiment of the imaging system of the invention can be used to gainfully improve efficiency of data collection in a unit of data-acquisition time through samples with thickness on the order of several tens of microns (as a non-limiting example, 30-50 microns) and, in doing so, reduce overall photo-bleaching of the sample due to reduced exposure time. Practical limitation of thickness of samples that can be advantageously imaged with the described hybrid polyfocal-stepping embodiment may be imposed by optical clarity of the imaged sample and the working distance of the objective lens. The advantages provided by such hybrid acquisition system include the ability to efficiently identify the locations of the 3D-sample features of interest and the overall 3D anatomical structure of the sample. This capability may prove advantageous in, for example, facilitating the localization of genetic sequences on chromosomes in 3D space with greater spatial accuracy and/or extended focal range, the identification of the relative distribution of chromatin, or the irregularity of the 3D shape of the nucleus.

Spectral Device

To obtain a spectrally-resolved imaging data, embodiments of the present invention may employ various strategies. General spectrally-selective devices that include interference filters, color-absorbing filters, a combination of a tunable birefringent liquid crystals (LCs) and a waveplate with crossed polarizing elements, acousto-optical filters (AOFs), electro-optical (EO) tunable filters, dispersive optics such as a diffraction grating operating in reflection or transmission, a prism, dichroic or polychroic mirrors, to name just a few examples, were described in reference to FIGS. 1A, 1B.

Figure 11A:
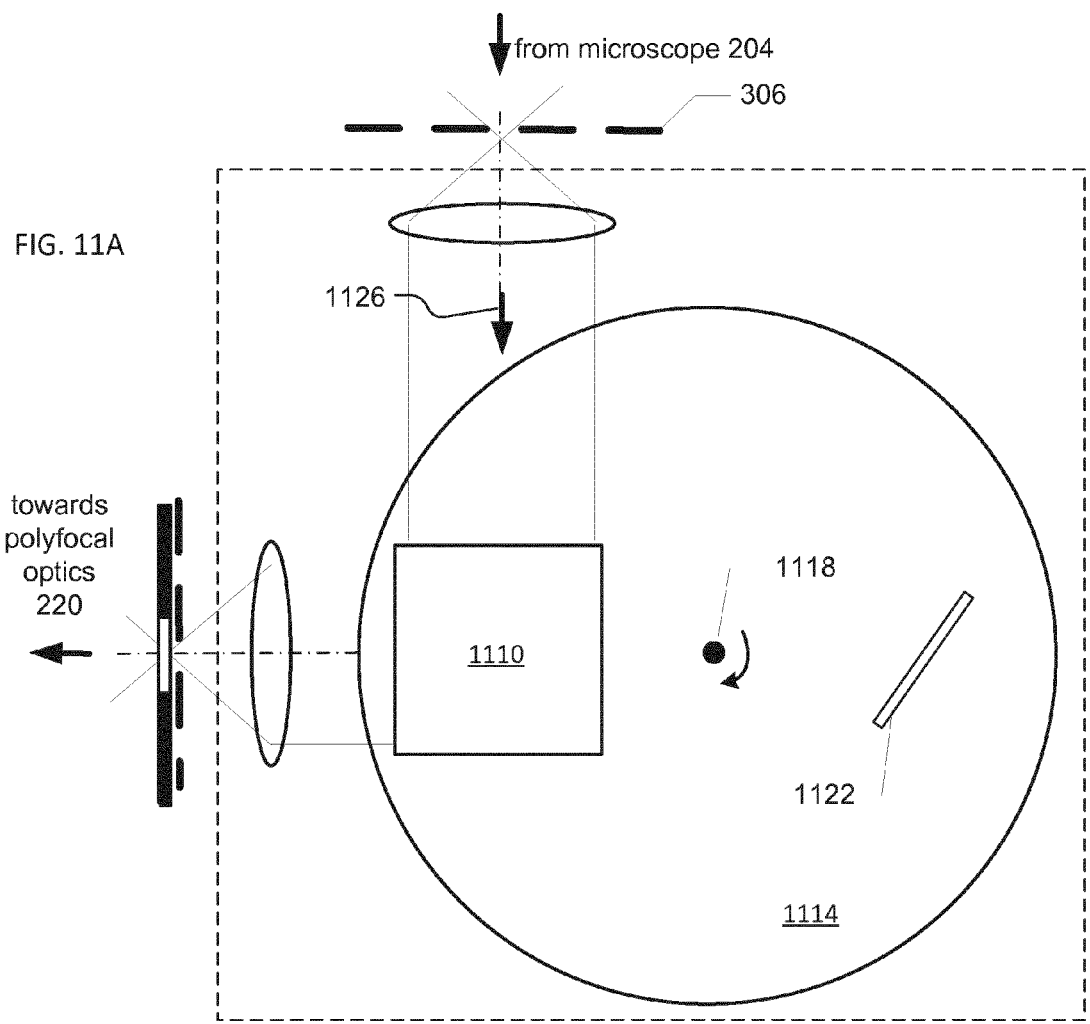
FIG. 11A is a schematic of an embodiment of a spectrally-selective portion of the system of FIG. 2.
Figure 11B:
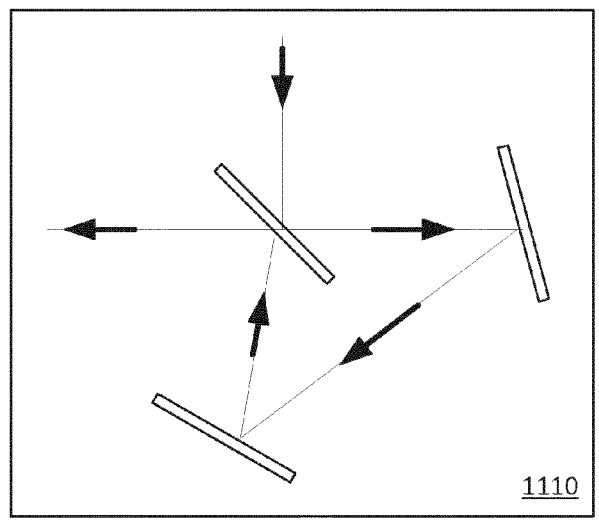
FIG. 11B is a schematic of a specific embodiment of a spectrally-selective portion of the system of FIG. 2 adapted as a Sagnac interferometer.

In specific embodiments, the spectral device 200 of FIG. 2 can be adapted to include an (optionally tunable) optical etalon or interferometers such as an (optionally tunable) Fabry-Perot, Michelson, Sagnac, Fizeau, or Gires-Tournois interferometer that ensures very high spectral resolution. It was also unexpectedly empirically found that an interferometric spectral device used as a spectrally-selective system of an embodiment of the invention provides higher light throughput for every wavelength transmitted through the spectral device for a unit of given acquisition time as compared to another spectrally-filtering element. Referring to FIG. 11A, an interferometric spectral device as part of the polyfocal imaging embodiment of the system of the invention causes encoding of the spectral information of light that has been transmitted through the spectral device into interferometric fringes superimposed onto the polyfocal image formed by the system. The interferometer 1110 is adapted, therefore, to operate as a Fourier Transformer by converting the spectral information contained in image-forming light delivered to the detector plane from a frequency domain to a spatial domain. By analyzing the spatial distribution of the interferometric fringes in the final image, the spectral distribution of the image-forming light is therefore recovered. In the embodiment of FIG. 11B, for example, a spectral device 1110 includes a Sagnac interferometer disposed on a support 1114. As shown in FIG. 11A, the support 1114 is rotatable around the axis 1118 to ensure that the spectral filter 1110 can be disengaged from the overall system and substituted with a spectrally-indifferent reflector such as a simple mirror 1122, for example, by a simple rotation of the support 1114 and to ensure that interference fringes in the final image on the detector plane can be introduced. Another advantage of using the interferometer such as a Sagnac or Michelson interferometer as a spectral device in an embodiment of the invention employed in Fourier Transform spectroscopy includes more efficient collection of signal data at low light levels (as in fluorescent spectroscopy, for example). Specifically, an improvement in signal-to-noise ratio is gained when taking multiplexed measurements rather than direct measurements (an effect known as Felgett advantage). When the interferometric spectral device 1110 is disengaged from the optical path (not shown in FIG. 11A, 11B), the multispectral imaging can be ensured with the use of a different spectral filter.

Reduction of Image-Acquisition Time

The acquisition rate of a conventional, serial image acquisition system is limited by several factors including at least (i) the step-rate of the spectrally-selective device multiplied by the number of exposures within a given spectral bandwidth (for multispectral imaging) or the exposure time multiplied by the number of exposures (for monochromatic imaging); (ii) the step-rate of a z-scanning unit multiplied by the chosen number of z-positions of the objective at which images of the sample are taken; and (iii) the computational time required to process spectral images acquired at different object planes. As was discussed in reference to FIGS. 3-5, 6, 7, 9, and 10, embodiments of the invention facilitate enhancement of the optical depth-of-field of a conventional microscope system and image multiple object planes without specialized instrument control and/or movement of a component of the system beyond a position in which a conventional microscope-based imaging system can capture an image of a single object plane. As a result, in a unit of image-acquisition time, a greater amount of imaging data representing different in-depth object planes is acquired with a polyfocal embodiment of the invention than that representing a single object plane and that is acquired with a conventional microscope image-acquisition system. Stated differently, a shorter interval of time is taken to acquire image data describing several object planes with a an embodiment of the polyfocal imaging system of the invention than with a conventional, sequential-acquisition system capable of imaging a single object plane at a time. This advantage is illustrated in FIG. 12 showing the graph 1210 of total acquisition time required for a conventional, single object-plane imaging system equipped with a z-stepping motor to collect hyperspectral data representing four object planes located ad different depth within the object. For comparison, a graph 1220 is shown that represents the time, as calculated, that is required for a polyfocal system of the invention equipped with four imaging channels (see FIG. 4) and an interferometer (see FIG. 11) to acquire the same imaging data. The spectral distribution of data defined 512 interferometric steps (exposures) of the tunable interferometer of the polyfocal system, where each step takes about 80 ms. Acquisition of the same data with a conventional system takes in excess of 100 sec seconds per object plane.

Figure 12A:
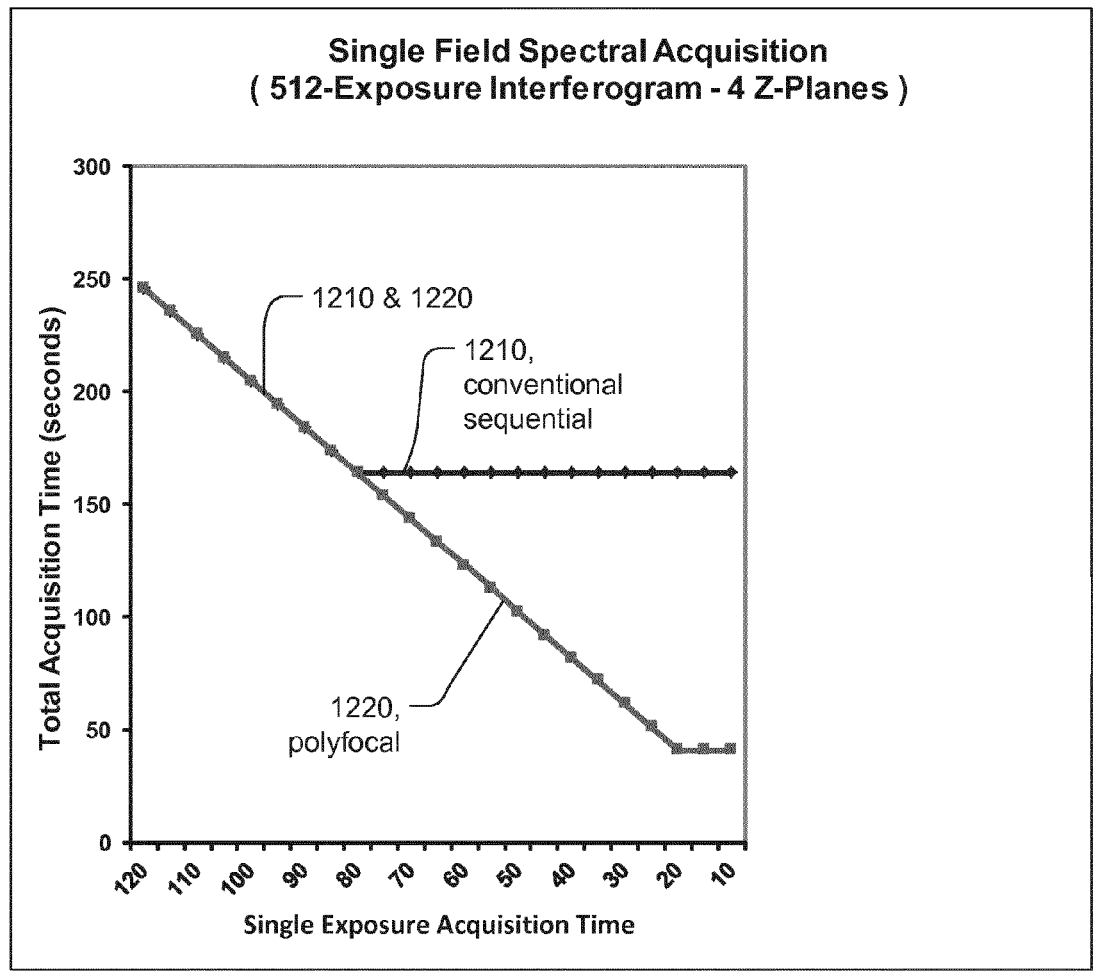
FIG. 12A is a graph illustrating the reduction of time of data acquisition carried out with an embodiment of the invention in comparison with data acquisition time required by a conventional microscope-based imaging system.
Figure 12B:
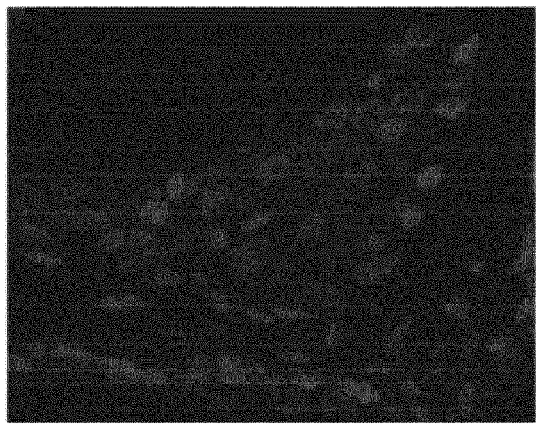
FIGS. 12B, 12C, 12D, and 12E are images of a biological tissue and corresponding schematics of system used in acquisition of these images that illustrate the degree of the sample-photobleaching effect achievable with the use of an embodiment of the invention and reduced in comparison with that resulting from the use of a conventional microscope-based imaging system.
Figure 12C:
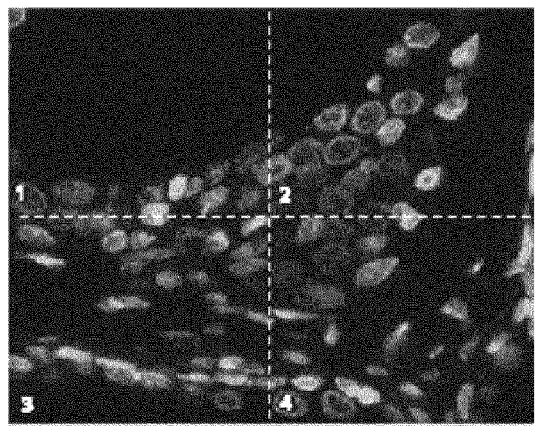
Figure 12D:
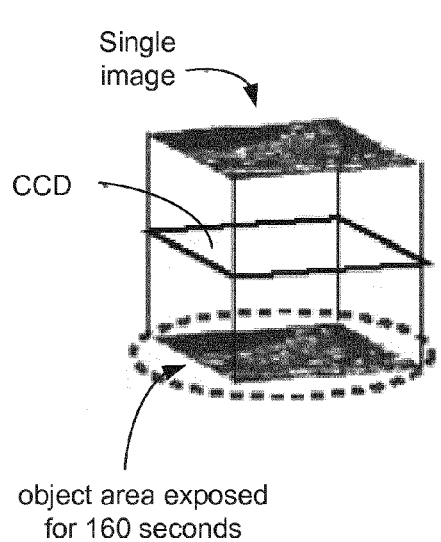
Figure 12E:
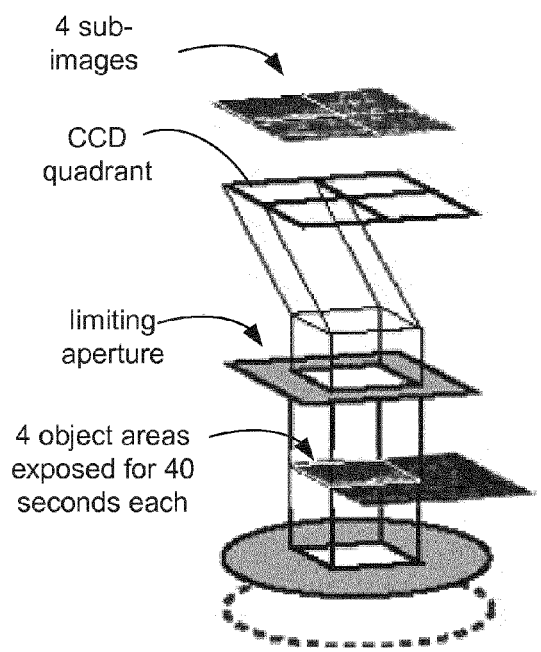

In further reference to FIGS. 8A, 8B and 12A, the photobleaching-reduction effects of multispectral image acquisition with the use of polyfocal imaging system of the invention are shown in FIGS. 12B and 12C. FIG. 12B illustrates an image of a DAPI-stained prostate tissue sample acquired, in an approximately 160 second exposure, within a FOV of a conventional system that was devoid of polyfocal capabilities of the present invention. The sketch describing this conventional arrangement is schematically shown in FIG. 12D. The degree of photobleaching of the sample corresponding to FIG. 12B is estimated to be about 75%. In contradistinction, the image of FIG. 12C is an image of the same sample acquired with a polyfocal embodiment of the present invention, in four consecutive steps, by imaging an approximately ¼ of the above-mentioned FOV in each of the consecutive steps on a corresponding quadrant of the detector. This example illustrates the use of an aperture in the field illumination path to restrict the illuminated area to only that smaller region which is being imaged through the polyfocal optical portion. The schematic related to this imaging arrangement is shown in FIG. 12E. It is understood that each of the ¼ FOV sub-images 1, 2, 3 and 4 of FIG. 12C required only a 40 second exposure, thereby reducing the overall degree of photobleaching of the sample to about 18.75%. The use of a smaller aperture in a plane that is conjugate to the field plane can be used to extend the depth-of-field of illumination such that the depth-of-field for excitation is increased. By reducing the angle of incidence for incidence (for example, via reducing a corresponding numerical aperture), a larger depth of uniform illumination flux can be realized along the beam axis. This consideration can help to ensure adequate excitation of fluorophores through the depth imaged with the polyfocal device.

Specific Examples of Hyperspectral Polyfocal Image Data Acquisition and Processing Multispectral imaging of a biological sample was carried out with an embodiment similar to that of FIG. 2, that contained a microscope system of FIG. 3, an embodiment of the spectral device including a Sagnac interferometer such as that of FIGS. 11A, 11B, and the polyfocal optical portion having four optical imaging channels and arranged according to the embodiment of FIG. 4. The following discussion, therefore, is presented in reference to FIGS. 2, 3, 4, and 7. To permit the four object planes to be imaged respectively onto the four quadrants of the single detector 224, the field aperture 406 was rectangularly shaped and sized to transmit the central 25% of the FOV provided by the optics of the embodiment. The optical characteristics of the steering mirrors 412A, 412B, 412C, 412D, 412E, 412F, 412G, and 412H, summarized in Table 1, were chosen to ensure that sub-images formed through the four optical imaging channels of the polyfocal optical portion have comparable levels of intensity.

TABLE 1

| | Mirror | | | | | | | |
|---|---|---|---|---|---|---|---|---|
| | 412A | 412B | 412C | 412D | 412E | 412F | 412G | 412H |
| T/R | ¾ | 0 | ⅔ | 0 | 0 | ½ | 0 | 0 |

The focal lengths $f_i$ of the adjustment lenses 428, 432, and 436 were appropriately chosen according to $$1/F_i = 1/f_i + 1/f_1 - [d/(f_1 f_i)]$$

where d is the geometrical distance between the lens 440, having the effective focal length $f_1$, and a portion of given ith focus-adjustment lens having an effective focal length $f_i$, and $F_i$ is the effective focal length corresponding to the ith optical channel. The differences in effective focal lengths among the optical imaging channels of the embodiment are calculated to correspond to increments of the DOF of the objective lens 330 multiplied by the magnification of the objective lens. For example, if the DOF in object space is 2 microns, and the magnification of an optical channel is 40×, then the target shift of the image plane at the CCD is 80 microns. In practice, therefore, some of the adjustment lenses 428, 432, and 436 were appropriately chosen to have negative optical power(s) and some to have positive optical power(s). As a result, such that the detector 224 registered, in corresponding quadrants, the sub-images 721A, 722A, 723A, and 724A such that one of the sub-images represented a chosen object plane, and the remaining three sub-images represented the object planes located at 2 microns below the chosen object plane, and at 2 and 4 microns above the chosen object plane. Aggregately, the registered sub-images spun the range of depth (along z-axis of FIG. 3), in the object space, of about 8 microns. The custom anti-reflection (AR) coated lenses were found to be appropriate for imaging at 40×NA=0.75 (the objective lens 330, a 2 micron depth-of-field).

Figure 13A:
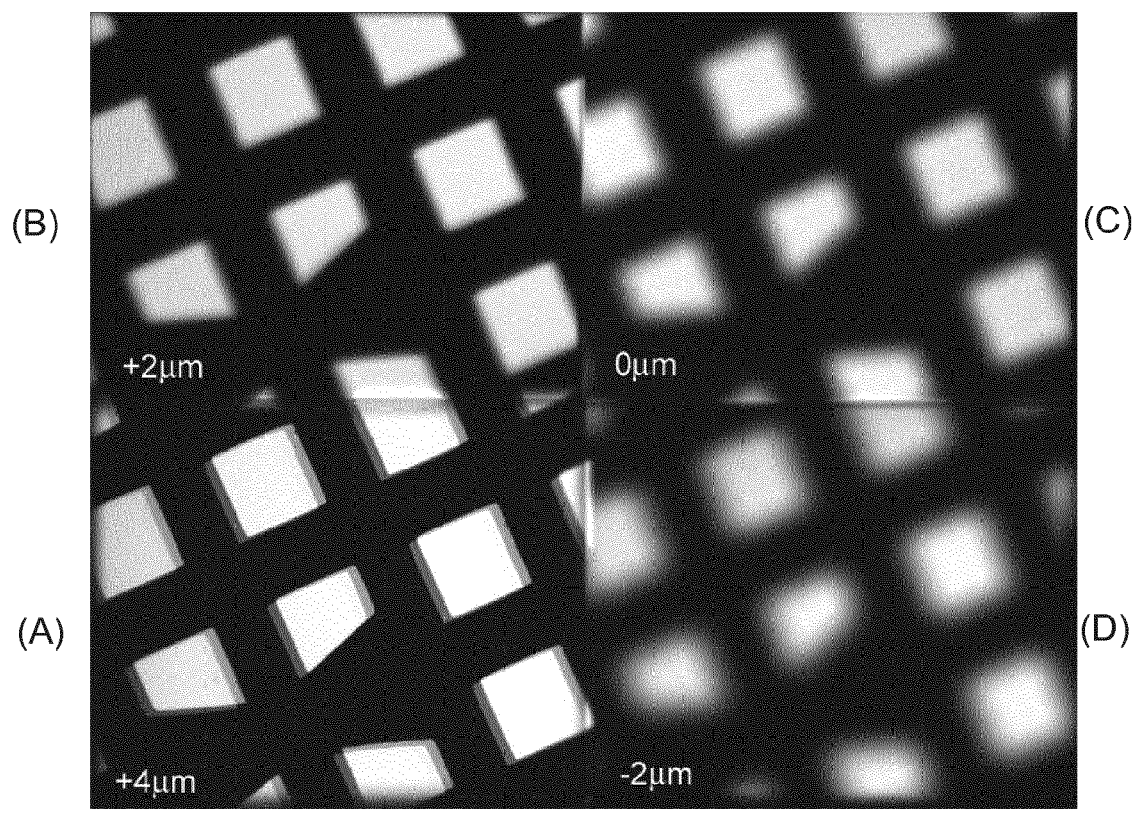
FIG. 13A presents four polyfocal images of a grid reference acquired with an embodiment of FIG. 5C.

FIG. 13A shows four polyfocal sub-images (A), (B), (C), and (D) of four object planes formed, simultaneously, by the four optical imaging channels of the embodiment of the imaging system of the invention in which the interferometer (used as a spectral device) has been disengaged, at 20× magnification. The imaged object included a thin metallic foil patterned as a grid and mounted on a transparent substrate for transmission light microscopy. The depth of filed corresponding to each of the images is 2 microns. In reference to the diagram of FIG. 6 it is appreciated that, aggregately, the four images of FIG. 13A represent an object space depth of 8 microns. In this image acquisition, the plane of best focus was chosen to correspond to image (A).

Figure 14:
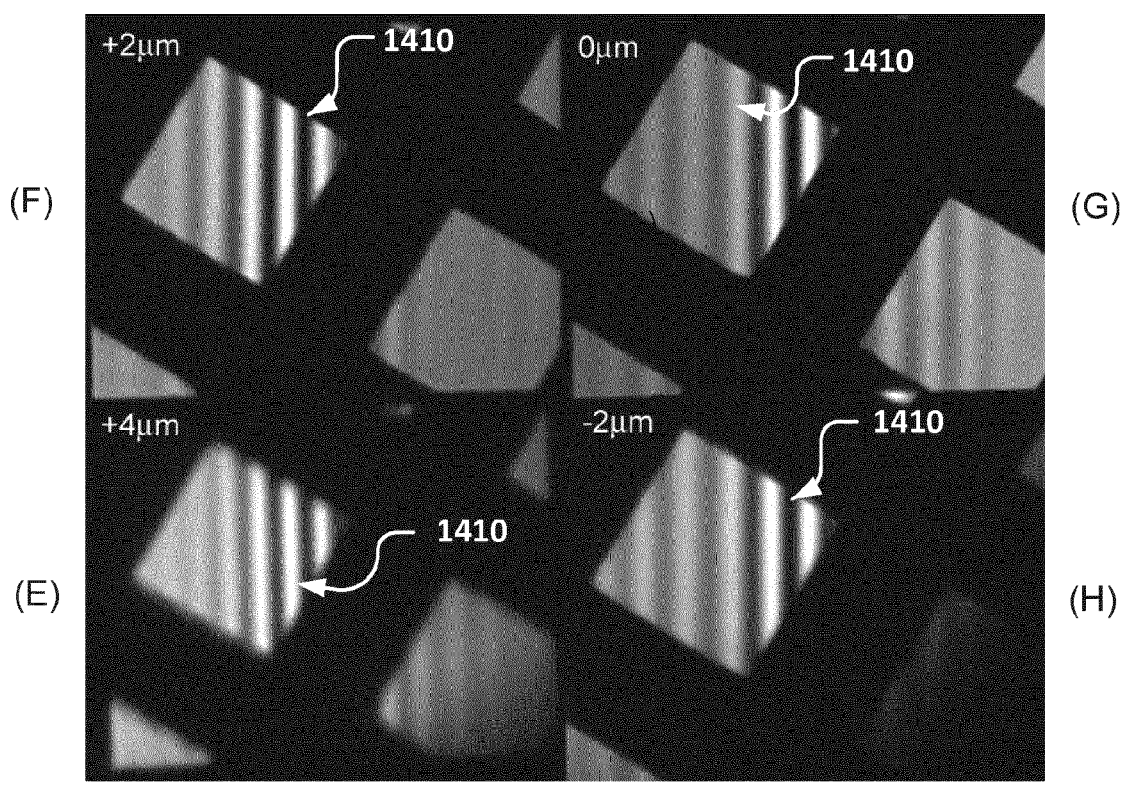
FIG. 14 presents four multispectral polyfocal images acquired with an embodiment of FIG. 2.

As a result of imaging of the same thin metallic foil grid object through a complete embodiment 200 of a polyfocal spectral imaging interferometer of the invention (that included both the Sagnac interferometer 1110 as a spectral device 220) and the polyfocal optical portion 400 as discussed above, the detector 224 registered the sub-images (E), (F), (G), and (H) of FIG. 14. The image (G) corresponds to the plane, in object space, that is substantially in focus. The images (F) and (H) represent the object planes shifted, with respect to that of the image (G), by 2 and −2 microns (above and below the object plane of the image (G), respectively). The image (E) represents an object plane located at about 4 microns above the object plane corresponding to the image (G). As a result of transforming of the spectral content of the imaging data into the spatial domain with the use of the Sagnac interferometer, as discussed above, each of the sub-images (E), (F), (G), and (H) of FIG. 14 contains vertical interference fringes 1410 indicating that the interferometer is present in the optical path. The analysis of the geometry of the interference fringes 1410 with an appropriately programmed computer processor allows to extract the spectral content of the images of FIG. 14. It is appreciated that images such as those of FIG. 14 represents a data set containing information about 4 different 2D-objects (i.e., 4 object planes) spatially-separated along a chosen direction and imaged at chosen wavelengths.

Figure 15:
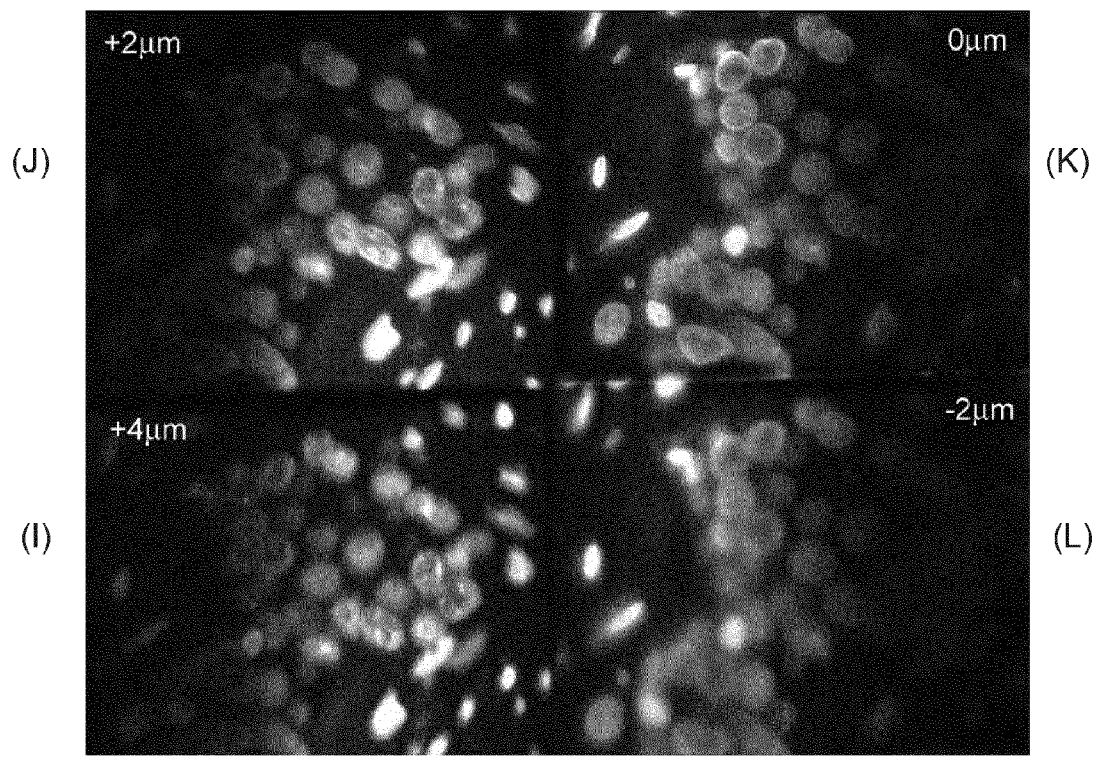
FIG. 15 presents four hyperspectral images of a quantum-dot marked prostate tissue acquired with the use of the embodiment of FIG. 2.

An embodiment of the invention was further used to acquire, in a single image acquisition cycle, hyperspectral imaging data representing a series of in-depth planes of a 3D prostate tissue sample labeled with Q-dots (QDs), as shown in FIG. 15. To effectuate the tissue labeling or targeting, the QDs are often functionalized with tissue-specific binding sites to selectively bind to a chosen portion of the tissue. For example, QDs may be used as inorganic fluorophore for detection of biological tissue components using fluorescence spectroscopy. Here, QDs are used as a components of a tissue molecule that causes this molecule to fluoresce in a way that specifically identifies the corresponding type of tissue components. By detecting the QD-specific fluorescence of the tissue sample at hand, a conclusion can be made about the biological structure of the tissue and/or the location of a particular component of the tissue.

Figure 16:
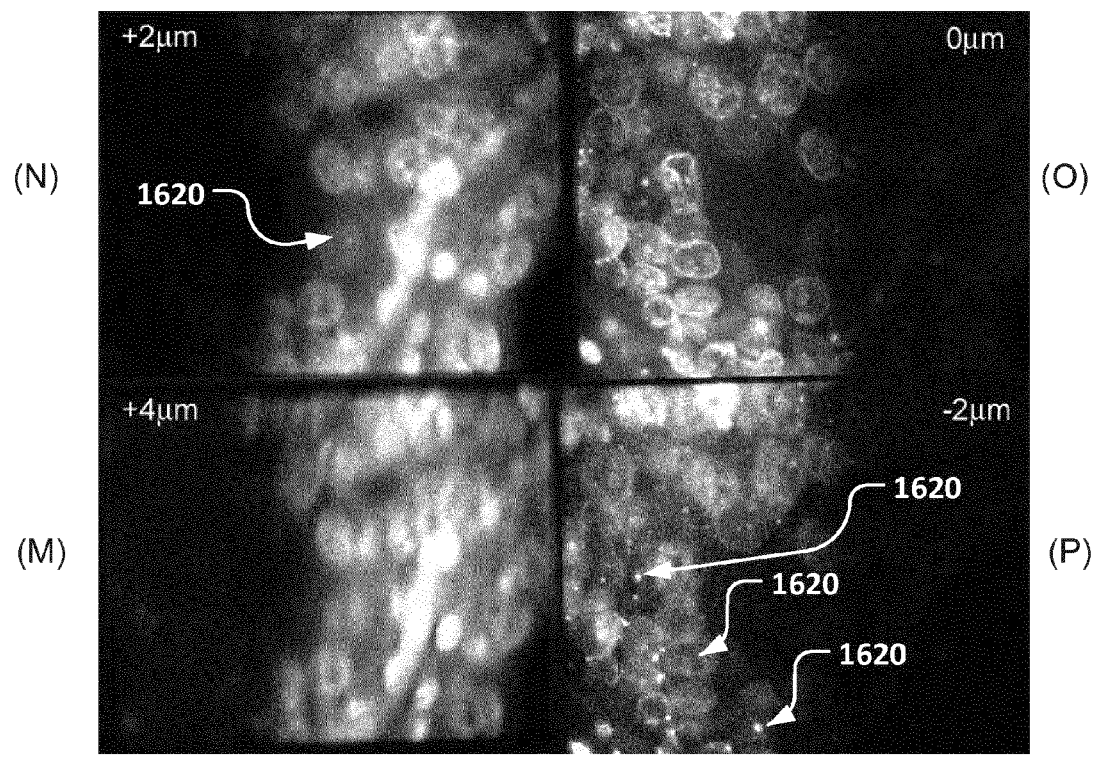
FIG. 16 presents four additional hyperspectral images of a quantum-dot marked prostate tissue acquired with the use of the embodiment of FIG. 2.

FIG. 16 illustrates four sub-images (M), (N), (O), (P) of different in-depth planes of a 3D prostate tissue sample acquired as discussed above, where different object features such as QDs associated with the nuclei 1620, for example, are distinguished at different depths in the object. A 2 micron depth of field for each image corresponds to the 40×NA=0.75 (the objective lens 330) imaging conditions with no overlap in depth of focus.

Figure 17:
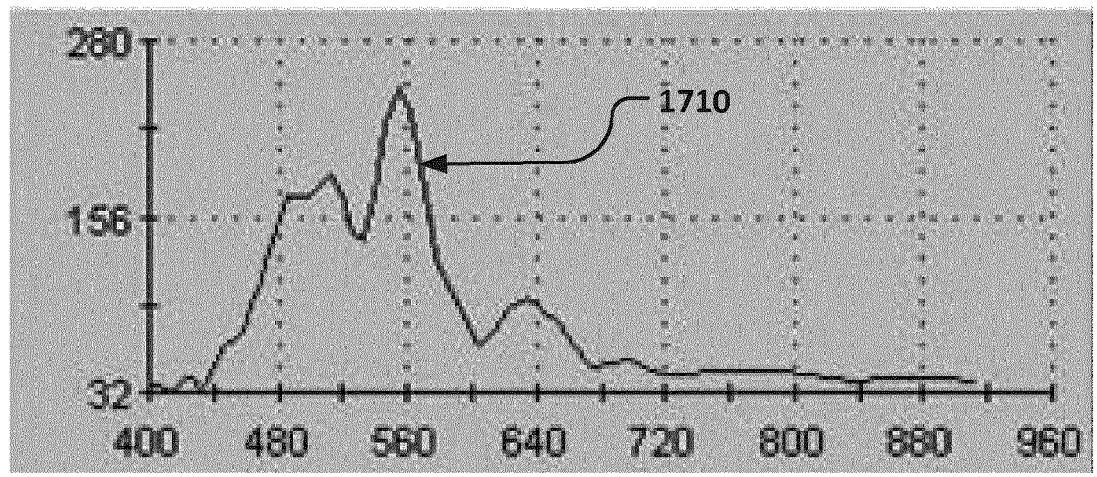
FIG. 17 is a graph showing a spectral trace corresponding to quantum-dot markers located at a sample as imaged in FIG. 16.

In case where different fluorophores (such as different species of QDs) are co-localized, the sub-images representing different planes of an object labeled with fluorescent markers (such as those of FIG. 16) can be further used to resolve the presence and contribution of the co-localized fluorophores. FIG. 17, for example, illustrates the sum (unprocessed) spectral trace derived from an average of spectra of light received from the markers in a 3×3 pixel area indicating co-localization of probes in the FOV corresponding to FIG. 16. The features of the spectral curve 1710 are consistent with spectral peaks of fluorescence corresponding to QD565, QD655, and DAPI counterstain, thereby indicating that the spectral information has been successfully decoded from the interferogram portion of the final image (such as the interferometric fringes 1410 of the image of FIG. 14, for example). Here, QD species emitting light in the vicinity of 565 nm is labeled as QD565, and that emitting light in the vicinity of 655 nm is labeled as QD655.

Figure 18:
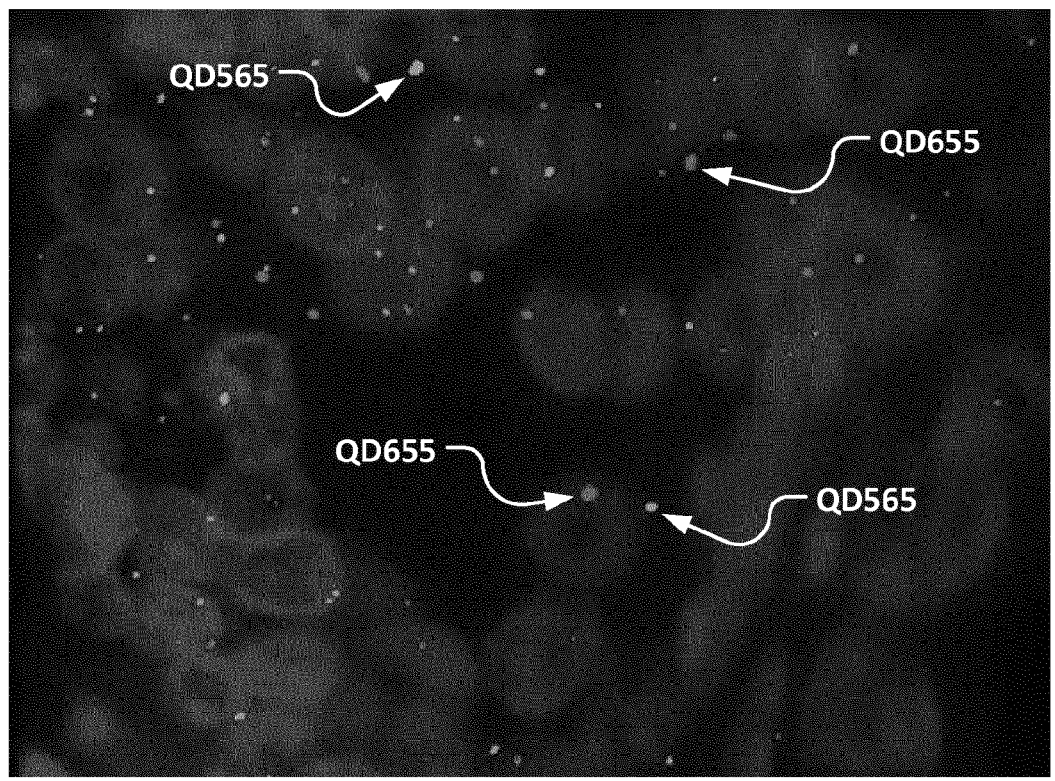
FIG. 18 is a composite image representing 3 overlapped spectrally-unmixed images of 3 different planes of a quantum-dot labeled sample of FIG. 16.

An embodiment of a computer program product of the invention, adapted for processing the imaging data acquired with an embodiment of the system of the invention, can be further used to facilitate (i) spectral unmixing (or decomposition) of data corresponding to different markers (such as QD565 and QD655, for example) that are imaged onto the same pixel of the detector, and (ii) resolving the presence of each marker and the relative amount of its contribution to the image. Spectral unmixing can be performed using linear methods known in the art or, in a specific embodiment, using a non-linear method described in a commonly assigned and co-pending U.S. Provisional Application No. 61/483,202 filed on May 6, 2011 and titled "Method and System of Spectral Unmixing of Tissue Images," the disclosure of which is incorporated herein by reference. The spectrally unmixed imaging data, acquired in each of the optical imaging channels of the system of the invention, are then used to form corresponding sub-images that represent different depths of the sample. These sub-images can be analyzed independently or, alternatively or in addition, these sub-images can be appropriately cropped, if required, and overlayed to form an ultimate 2D image representing a projected, onto a single image plane, image of the 3D biological object sampled at identified object planes. An example of FIG. 18 shows such ultimate image resulting from an "overlay" of 3 spectrally-unmixed sub-images representing 3 different object planes (respectively corresponding to 3 different depths) of the object of FIG. 16. To obtain the image of FIG. 16, a set of imaging data representing three out of four planes (depths) of the object, acquired at wavelengths that were pre-defined with an interferometer of the embodiment of the invention, was spectrally unmixed as known in the art and overlayed.

Additional Features

Embodiments of the invention provide additional advantageous features, characteristics, and capabilities such as, for example, A) enablement of automated axial positioning of the polyfocal volume that is being imaged with respect to the focal plane of the objective lens; and B) mitigation of optical fore-shortening during image acquisition under index-mismatching conditions.

Autofocusing Capability.

Figure 13B:
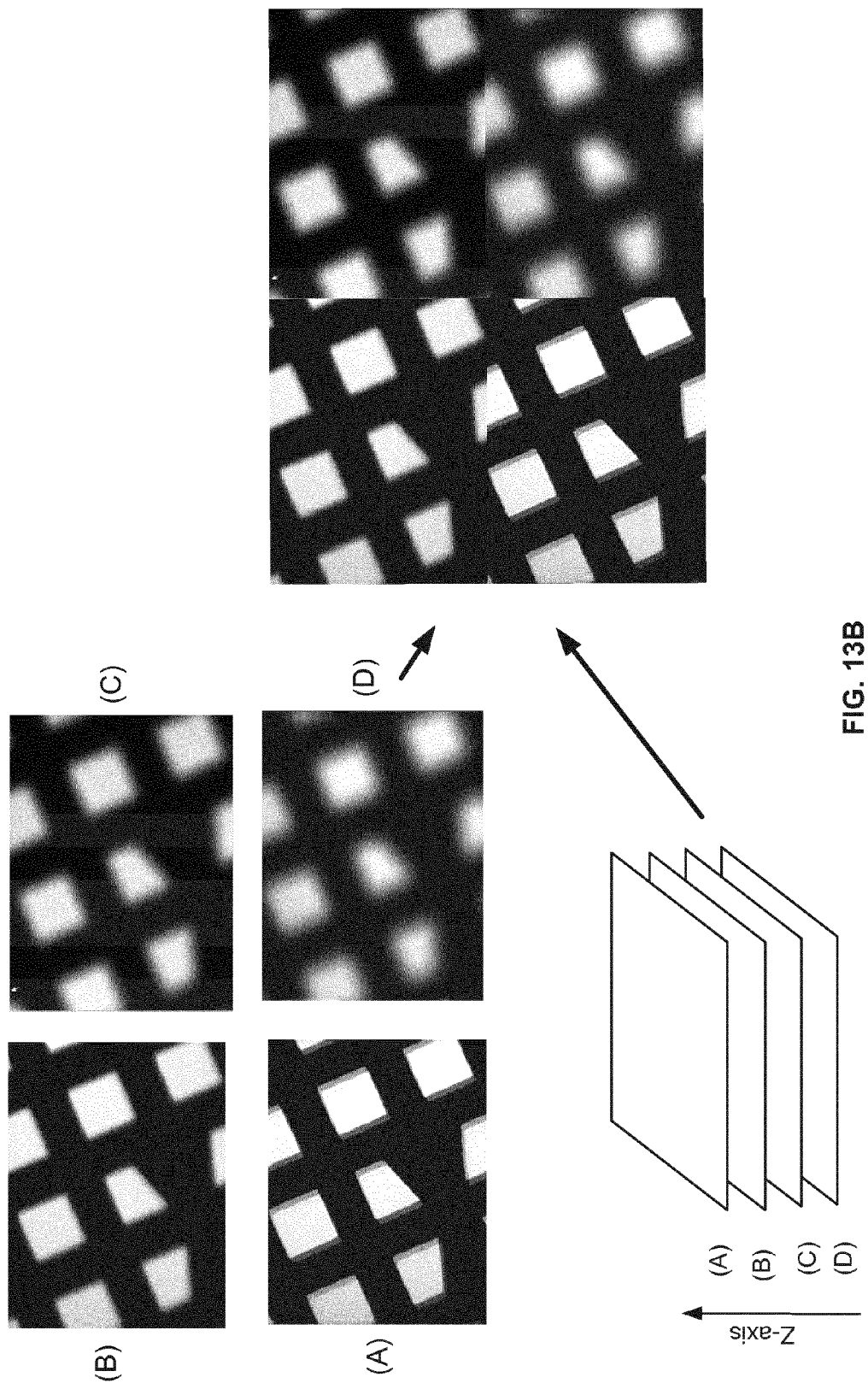
FIG. 13B is an illustration of order of acquisition and the adjoining positioning of the images of FIG. 13A on the detector.

In one example, the use of hybrid-polyfocal embodiment of the imaging system of the invention (i.e., the embodiment including both the polyfocal optical portion such as portion 400 of FIG. 4) and the electromechanical z-stepping means can be used to effectuate autofocusing during the acquisition of imaging data (whether with the use of a spectral device as part of the system, see, for example, FIG. 2, or with a spectral device being disengaged, as shown in FIG. 5C). A combination with an automated filter turret or an emission filter wheel could be leveraged to provide a wavelength-resolved autofocusing capability. In further reference to FIGS. 5C, 13A, and 13B, for example, the imaging data sets corresponding to sub-images (A) through (D), which represent different object planes of a grid standard element acquired with the use of the embodiment of FIG. 5C, are compared in pairs to devise a metric or figure of merit representing a change of a degree of blurring from one sub-image to another. In one embodiment, a comparison of the data sets includes a determination of a pixel-by-pixel difference of the imaging data and a creation of difference-sub-images corresponding to the difference image data sets. The metric defining the degree of blurring includes a value of intensity averaged over the pixels of such difference sub-images. For example, Table 2 summarizes the data representing difference sub-images (BA)=(B)−(A), (CB)=(C)−(B), and (DC)=(D)−(C) obtained, respectively, by subtracting respectively corresponding imaging data sets.

TABLE 2

| | Subtracted Sub-Images | | |
|---|---|---|---|
| | (BC) = (B − A) | (CB) = (C) − (B) | (DC) = (D) − (C) |
| Sum of intensity values over all pixels (~metric 1) | 2,364,927 | 3,241,436 | 4,941,410 |
| Average value of pixel intensity (~metric 2) | 8.1 | 11.1 | 17.0 |

Figure 19:
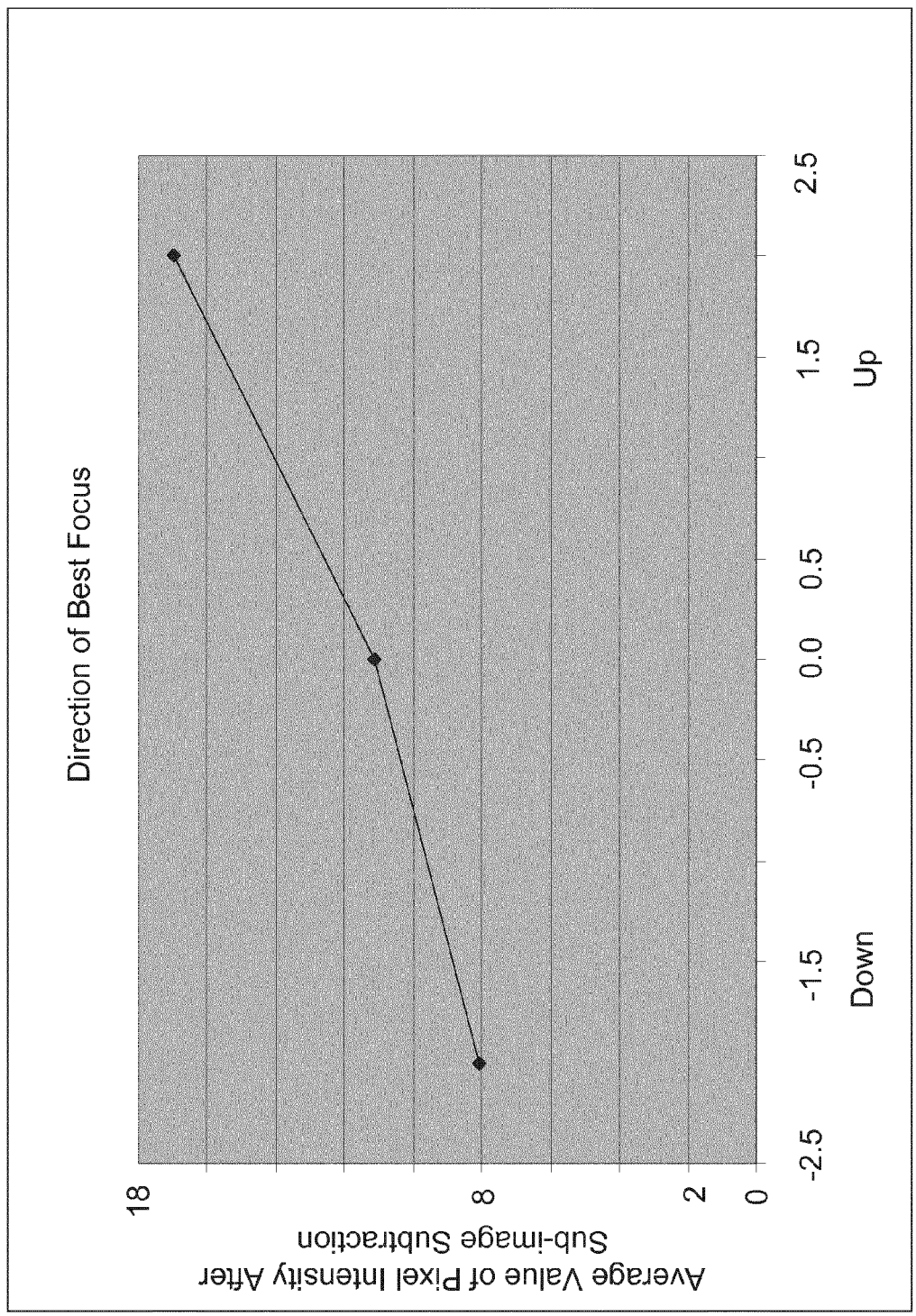
FIG. 19 is a graph illustrating a concept of optical-system autofocusing the implementation of which embodiments of the present invention facilitate.

It is appreciated that the value of the derived metric corresponding to an object plane that has been imaged while located in the focal plane of the objective is the highest among all of the determined metric values. In one embodiment, the metric can be defined an a sum of intensity values across all pixels of a "difference" sub-image. In an alternative embodiment, the metric is defined as an average value of pixel intensity. Therefore, based on the change in the derived metric values, a processor of the system of the invention can determine a direction of movement of the microscope objective with respect to the sample that would be required to arrive, from the current position of the objective, at an object plane that has been imaged with least amount of blur (or defocus). An example of the automated determination of the direction of "best focus" corresponding to FIGS. 13A, 13B, and Table 2 is illustrated in FIG. 19. In this example, to place the microscope objective at a point where it was when acquiring the image of the object plane that has been optimally focused, the objective should be moved in such a direction that is characterized by increase of a metric value determined, in real time, by the appropriately programmed processor.

In a related embodiment, alternative venues of characterizing the change in sub-images representing sequentially imaged object planes can be employed, such as, for example, (i) determination of contrast of image portions define by adjacent pixels; (ii) spectral analysis; (iii) histogram analysis; (iv) variance analysis; (v); Brenner's method; (vi) Range method; and Mendelsohn/Mayall method, to name just a few.

The above-described embodiment of a method for autofocusing of the imaging system of the invention can be used with either a darkfield or a brightfield microscope system that is equipped with a motorized stage adapted to automatically or manually change a distance separating the microscope objective and the sample being imaged (For example, to automatically reposition a element providing support for the sample, with respect to the objective). In particular, such change of working distance may be effectuated in order to co-locate an image plane in which a chosen sub-image is formed with the plane of the photodetector. In the case of sample thickness variations or when the sample is tilted, the autofocusing capability may be used to select sample regions of high focal contrast from multiple object planes and, by processing the corresponding image data, selectively "merge" the images of these regions into one continuous image having high contrast. The autofocusing capability may be used to select high-contrast targets, having chosen spectral characteristics (for example QDs fluorescing in the green portion of visible spectrum) from an object planed that has been imaged with high contrast. Additionally, this capability can be employed for compensation of various imaging shortcoming such as, for example, chromatic aberrations, by merging object planes having high contrast in defined spectral regions. One example of such merger include a merger of image regions having high contrast in red portion of the spectrum with those having high contrast in the green region of the spectrum.

Index-Matched Imaging vs. Index-Mismatched Imaging.

Embodiments of a system and method of the present invention can be used advantageously for accurate acquisition of imaging data representing object planes (located at different depths within the object) when the effective refractive index characterizing the object is different from (for example, higher than) the refractive index of the medium for imaging of which a given microscope objective has been optimized. It is recognized that a microscope objective designed to operate in air is intended to be used for imaging at a single position along the z-axis (for example, at a position corresponding to the sample/coverslip interface), and that when such objective is used for imaging of a sample having refractive index higher than that of air, the measurements representing axial position of a object plane being imaged are not accurate (and the use of the oil-immersion objectives is preferred). This error is caused by index mismatch between the incident medium (air) and the medium being images (sample) and manifests in apparent "stretching" of the ROI being imaged as the location of such ROI inside the sample increases.

Figure 20:
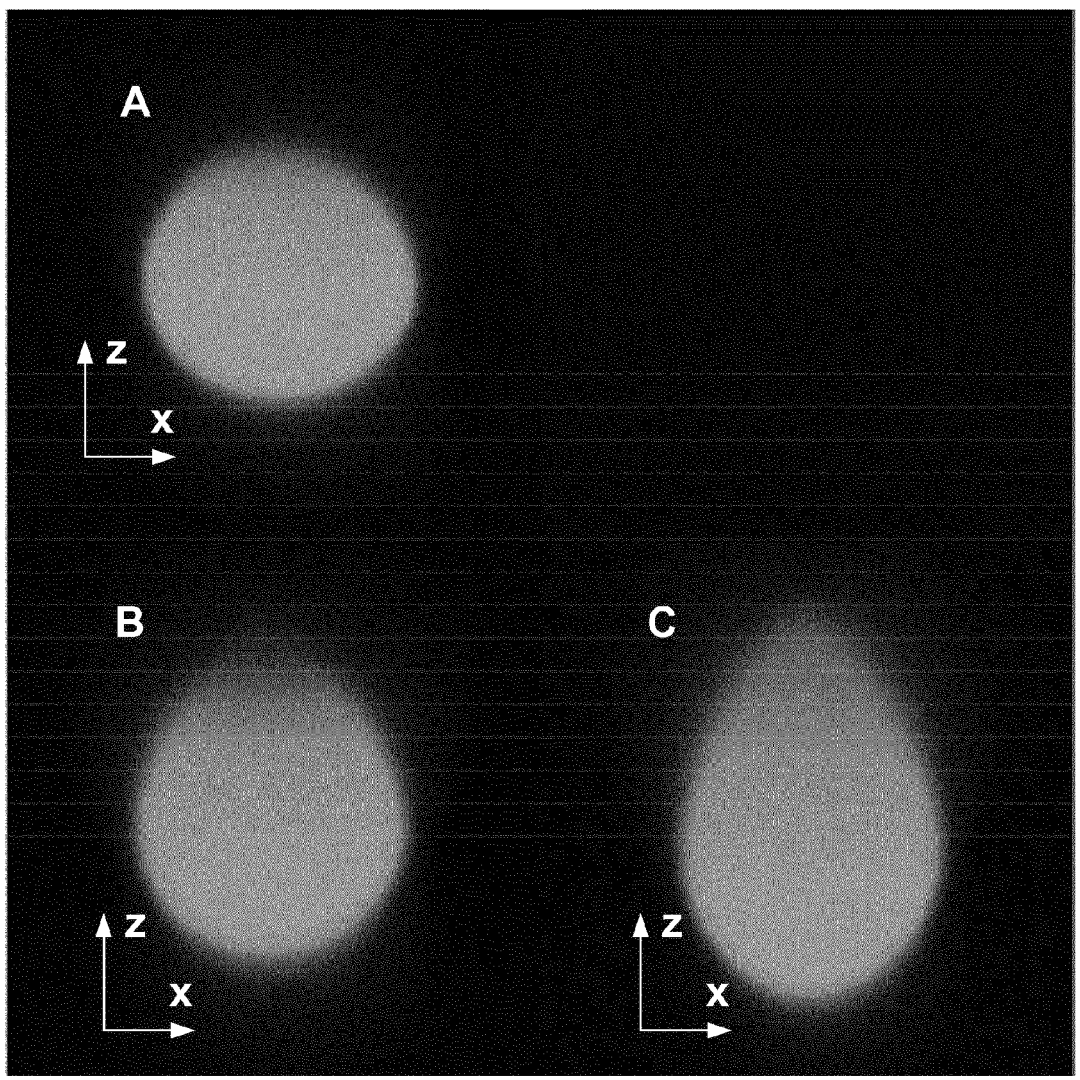
FIGS. 20, 21A, and 21B present images illustrating optical aberrations resulting from the use of a conventional microscope-based system for spectral imaging of a sample under index-mismatched conditions, and the advantages provided by the use of an polyfocal-imaging embodiment of the invention under the same conditions.
Figures 21A, 21B:
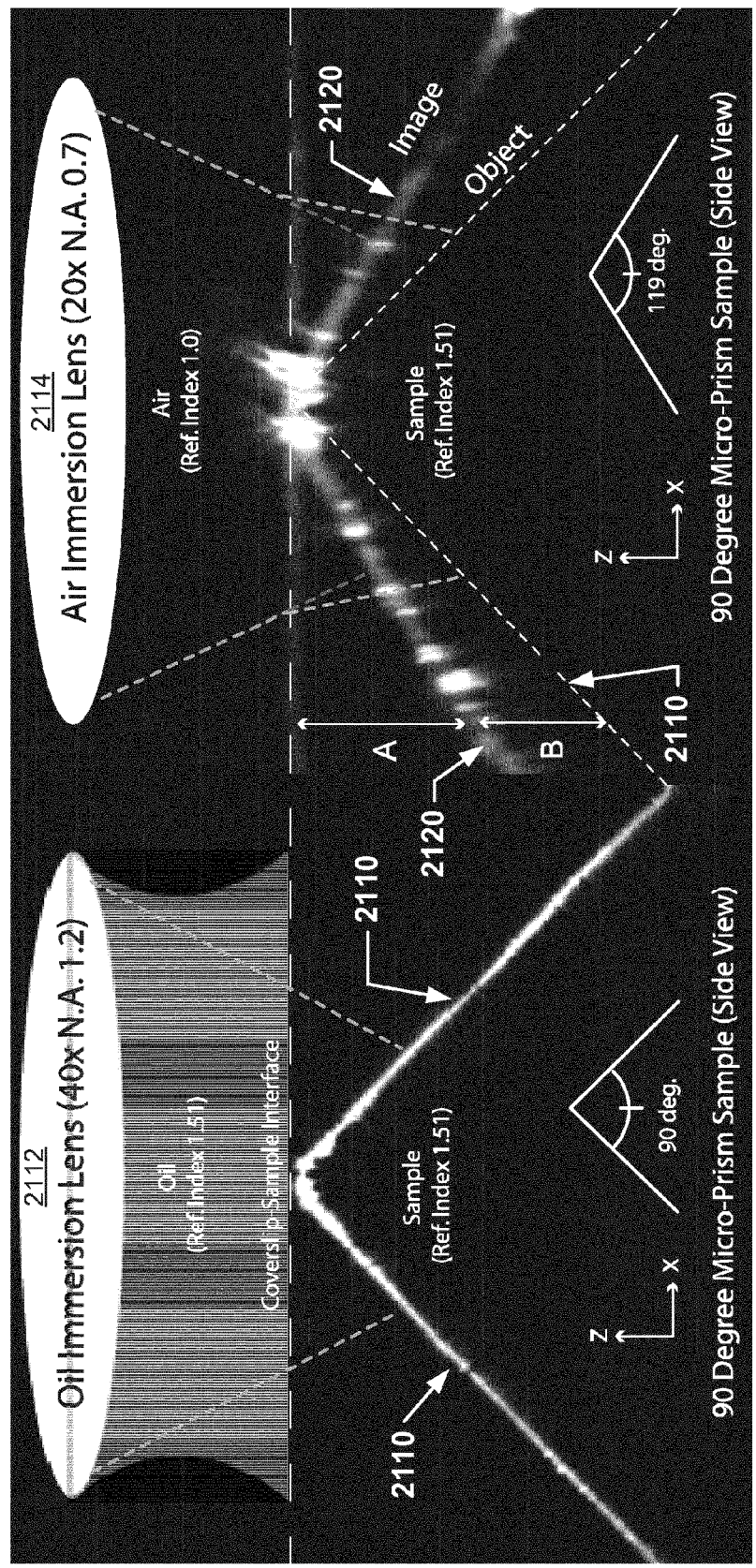

This aberration is easily understood from application of Snell's law and schematic illustrations presented in FIGS. 20, 21A, and 21B. FIG. 20 shows three images of a target fluorescent spherical bead (a fluorescent calibration microsphere having a diameter of about 10.2 microns) disposed under the cover slip and imaged with an oil-immersion objective that is mounted in the following media: index-matched oil (index of 1.51, image A); index-mismatched glycerol (index of about 1.42; image A); and index-mismatched water (index of about 1.3; image C). The apparent aberration of the image (the deviation of the shape of the image of the bead from the expected circular shape) along the axis direction (z-axis) increases with increase in refractive index-mismatch. Similarly, and in reference to FIGS. 21A and 21B, in the case when a objective, designed for imaging in air, is used to image a histological specimen (having a refractive index greater than that of air), the imaged features of the sample are progressively optically fore-shortened (compressed in the image) as the depth of the object plane that is being imaged increases. FIGS. 21A and 21B illustrate schematically, in side view, imaging of a 90-degree glass (n~1.51) reflective prismatic element (the boundary of which are denoted with a line 2110) under index-matched and index-mismatched conditions, respectively. Imaging under index-matched conditions was carried out with an oil-immersion lens (2112, 40×, NA=1.2) immersed in oil (n~1.51) on the coverslip above the sample. Imaging under index-mismatched conditions, on the other hand, was effectuated in air with a lens 2114 designed for imaging in air (20×, NA=0.7). Conventionally, the reconstruction of the imaging data acquired representing different object planes that have been imaged with the use of the z-stepping repositioning of the microscope objective is carried out under the assumption that the separation between the sequentially-images object planes is the same as the separation between the sequential positions of the objectives. In other words, conventional data processing is carried out under the assumption that the geometrical path associated with imaging is the same as the optical path. This assumption, however, is practically limited to the index-matching conditions (see FIG. 21A). When the optical path is altered by index-mismatch, such as in the case illustrated in FIG. 21B, for example, where the indices of the incident medium (air) and the medium being imaged (glass prism) are substantially different, z-stepping causes dimensional distortions in the reconstructed image data. The aberration resulting under index-mismatched imaging conditions is indicated in FIG. 21B by (i) the deviation of line 2120 representing a boundary of the image of the prismatic element from the boundary 2110 of the prismatic element itself, shown in FIG. 21B with a dashed line; and (ii) the change of the apex angle (~119 degrees) of the image of the prism as compared to that (90 degrees) of the prism itself. As shown in FIG. 21B, the imaged prism (indicated by the boundary 2120) appears to be "compressed" in the direction of scanning (z-axis). The value of the measurement error depends both on the depth of imaging and the refractive index of the sample, which significantly complicates calibration of the imaging procedure. The measurement error illustrated by FIG. 21B was determined to be about 38% of the depth of imaging (distance B, as measured from the coverslip/sample interface).

Figure 22A:
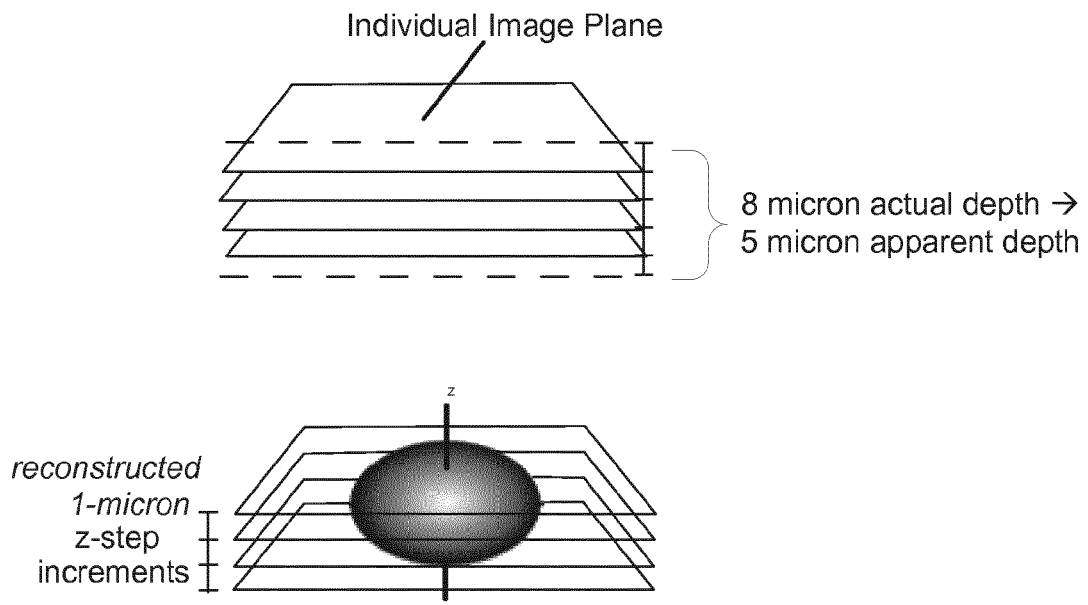
FIGS. 22A and 22B are schematics illustrating optical aberrations resulting from the use of a conventional microscope-based system for spectral imaging of a sample under index-mismatched conditions, and the advantages provided by the use of an polyfocal-imaging embodiment of the invention under the same conditions.
Figure 22B:
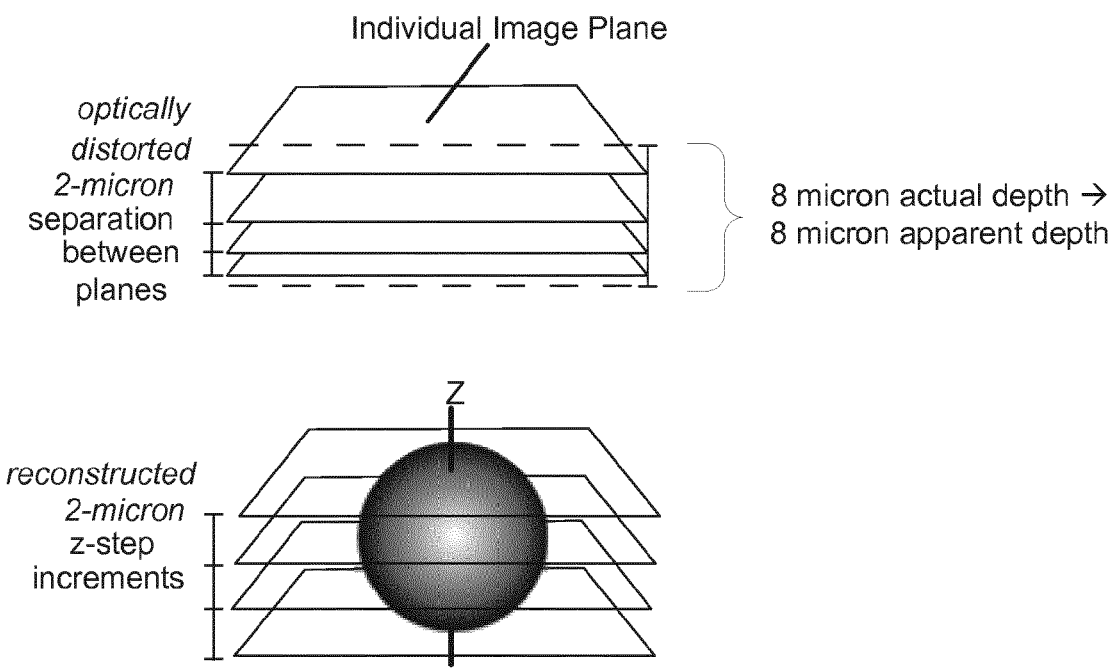

FIG. 22A offers additional illustration to aberration (optical fore-shortening of the reconstructed image) arising from imaging of the 3D sample under index-mismatched conditions. It is recognized that air-immersion imaging is preferred for spectral imaging of pathology specimens because is afford the higher depth of field, larger FOV, and ease of slide/sample handling. The use of embodiments of the present invention including a polyfocal optical portion mitigates the above-discussed measurement error, because the data representing changes in axial positioning of the microscope objective (along the z-axis) is derived in the image space rather than in the object space. When using the polyfocal imaging in accord with embodiments of the invention, the separation(s) between image planes and the image data corresponding to these planes are subject to the same optical path aberrations. As a result, during the image reconstruction procedure, these common aberrations are equally offset, as shown schematically in FIG. 22B.

The above-described aberration-compensating capability of the polyfocal imaging system and method of the invention may be useful for determination of pathological conditions in tissue, because such capability facilitates more accurate measurements of relative distances in 3D space. In addition, because the polyfocal optical portion of the system is not subject to error of electromechanical positioning of the microscope objective, the relative position of object planes is inherently more precise under index-mismatched conditions, in contradistinction with the conventional imaging systems that are currently employed in spectral FISH image acquisition, for example.

One of the examples of practical application of the described embodiments of the invention includes the enablement of pathology determination with extended depth of field, on formalin-fixed, paraffin embedded tissue. Because of the unique ability of the embodiments to acquire multiple focal planes simultaneously, the extended depth of field images in brightfield ISH or single or dual channel fluorescence or multi-modal brightfield-rendered context visualization ('pseudo-brightfield') could be produced in real time to permit navigation and convenient photo documentation with extended depth of field. Fast deblurring or extended depth of field processing of images may be implemented in such a way as to enhance the ability to perceive tissue and signal detection without defocus blur. This ensures higher quality experimental results over what is visible directly through eyepieces or on real-time display with a conventional streaming CCD camera. Embodiments of a method implementing multispectral imaging with the use of a system of the invention save the temporal overhead (conventionally associated with repeating the step-wise spectral acquisition multiple times, each at a different focal plane), as was discussed in reference to FIGS. 12A, 12B, 12C. Such improvement this is particularly relevant under conditions where the exposure time for polyfocal acquisition is shorter in duration than that corresponding to the spectral acquisition step rate or camera readout rate.

While the invention is described in reference to the examples of specific embodiments, it will be understood by those of ordinary skill in the art that modifications to, and variations of, the illustrated embodiments may be made without departing from the inventive concepts disclosed herein. For example, although some aspects of a method of the invention have been described with reference to a flowchart, those skilled in the art should readily appreciate that functions, operations, decisions, etc. of all or a portion of each block, or a combination of blocks, of the flowchart may be combined, separated into separate operations or performed in other orders.

Figure 23:
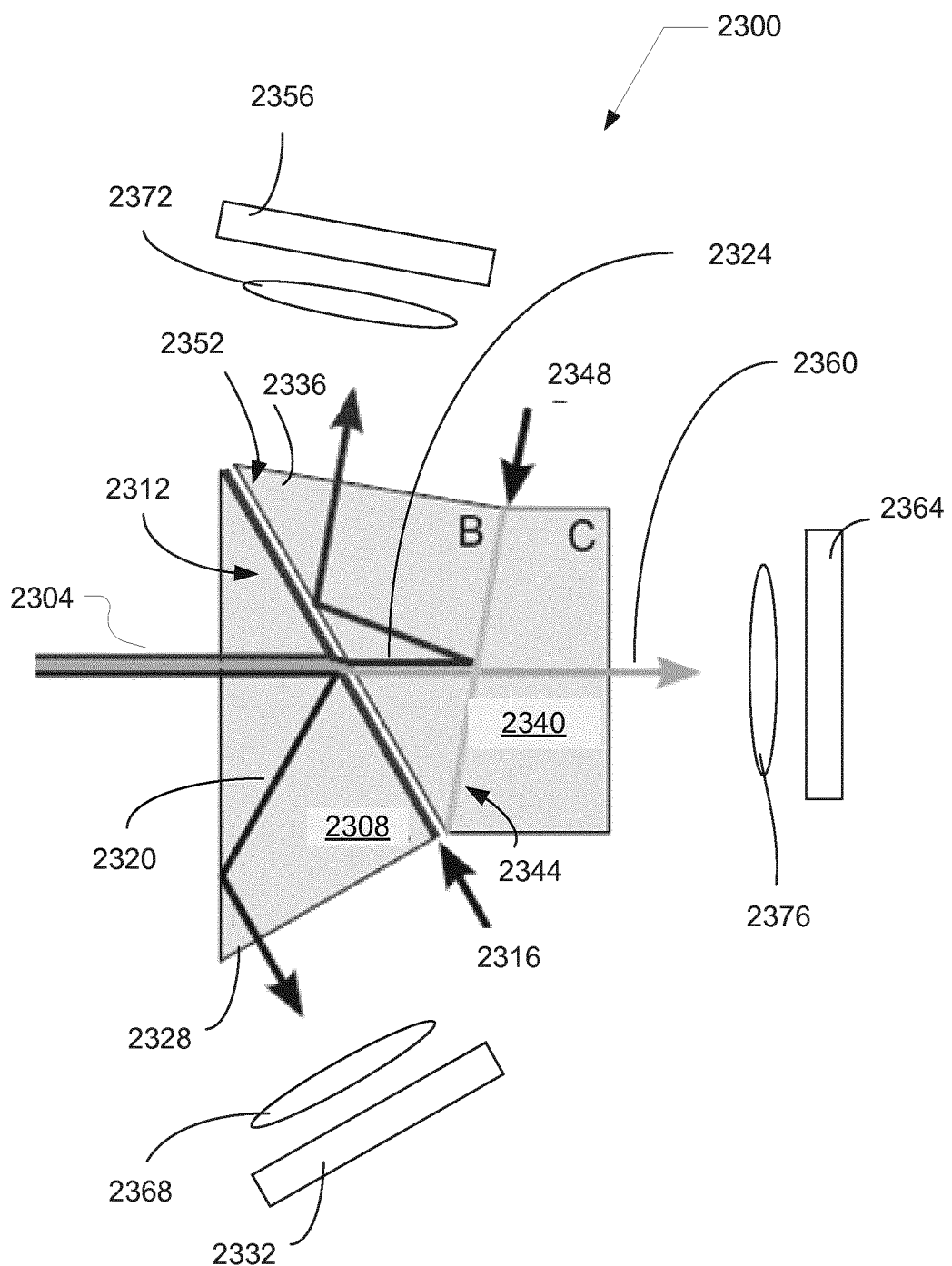
FIG. 23 is a schematic of an alternative polyfocal optical portion for use with an embodiment of the present invention.

Moreover, while the embodiments are described in connection with various illustrative data structures, one skilled in the art will recognize that the system may be embodied using a variety of data structures. While specific values chosen for embodiment of the invention have been are recited, it is to be understood that, within the scope of the invention, the values of all of parameters may vary over wide ranges to suit different applications. For example, alternative implementations of the polyfocal optical portion 220 of the embodiment 200 of FIG. 2 may include pyramid-like shaped mirrors and/or prismatic elements; optical beam-splitting to effectuate a plurality of optical image-forming channels may include polarization-based and/or wavelength-based beam division and splitting. Multiple detectors can be used (as the element 224 of FIG. 2) to increase the FOV, the readout bandwidth, or to enable complex beam-splitting schemes that facilitate high-speed imaging data acquisition. A specific alternative embodiment 2300, of the polyfocal optics and optical detector portions of the imaging system according to the invention, is shown in FIG. 23. In comparison with the embodiment 200 of FIG. 2, the embodiment 2300 is configured to receive light 2304, for example from the spectral device such as the device 220. The beam of light 2304 traverses a prism 2308 and is further divided at a facet 2312 of the prism 2308, which facet is optionally coated with the thin-film coating 2316 facilitating a predetermined ratio of intensities of a reflected beam 2320 and a transmitted, through the facet 2312, beam 2324. The reflected beam 2320 further undergoes total internal reflection (TIR) on another facet of the prism 2308 and exits through a side facet 2328 towards a detector 2332. The transmitted portion 2324 of the input beam 2304 enters another prism 2336, which adjoins a third prism 2340 along an interface 2344 (optionally coated with a thin-film coating 2348), and, after a partial reflection at an interface 2344 and a TIR at an interface 2352 of the prism 2336 exits towards a detector 2356. The remaining portion 2360 of the beam traverses the prism 2340 and is further registered by a detector 2364. Adjustment lenses 2368, 2372, and 2376 respectively associated with the detectors 2332, 2356, and 2364, are adapted to perform functions similar to those of the adjustment lenses 428, 432, and 436 of the embodiment of FIG. 2. In one implementation, the beam-splitting interfaces 2312/2352 and the corresponding coating 2316 are configure to ensure that the ratio of intensities of the beams 2320 and 2324 is about 33/67; and the mean-splitting interface 2344 and the corresponding coating 2348 are appropriately configured to ensure that the beamsplitting at the interface 2344 is approximately 50/50.

Furthermore, disclosed aspects, or portions of these aspects, may be combined in ways not listed above. Accordingly, the invention should not be viewed as being limited to the disclosed embodiment(s).

What is claimed is:

1. An optical imaging system having a plurality of image planes, the system comprising:
    a microscope configured to image an object to a first plane;
    a spectral device having an input and output and adapted to receive, at the input, an image formed by the microscope at the first plane and to produce, at the output, a light distribution comprising spatially-coded spectral content of the image formed by the microscope at the first plane; and
    a beam-splitter device in optical communication with the spectral device, the beam-splitter device having an input optical axis, including a plurality of optical channels respectively corresponding to the plurality of image planes, each of the optical channels from the plurality of the optical channels being adapted to re-image the light distribution onto a corresponding image plane such as to form a corresponding image representing a corresponding layer of the object located at a corresponding depth within the object.

2. The system according to claim 1, wherein the spectral device includes an interferometer.

3. The system according to claim 1, wherein the beam splitter device includes adjustable mirrors disposed in a spiral and staircase-like relationship with respect to the input optical axis of the beam splitter device.

4. The system according to claim 1, wherein a portion of said image representing a corresponding layer of the object from the plurality of images represents geometrically-coded spectral content of said corresponding layer of the object.

5. The system according to claim 1, further comprising a photodetector configured to detect images representing layers of the object located at different depths within the object.

6. The system according to claim 1, wherein said microscope has a microscope stage, configured to receive said object, and a positioner configured to change a distance separating a microscope objective from said microscope stage.

7. The system according to claim 6, further comprising a photodetector configured to detect images representing layers of the object located at different depths within the object, and wherein, when said object is located at the microscope stage, an activation of the positioner causes at least one of image planes corresponding to the plurality of optical channels coincide with a plane of said photodetector.

* * * * *